US 6,534,531 B2
(12) United States Patent
Kimball et al.

(10) Patent No.: US 6,534,531 B2
(45) Date of Patent: *Mar. 18, 2003

(54) METHODS FOR PREVENTING AND TREATING ALOPECIA INDUCED BY CHEMOTHERAPY OR RADIOTHERAPY

(75) Inventors: S. David Kimball, East Windsor, NJ (US); Kevin R. Webster, Yardley, PA (US); David K. Bol, Langhorne, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/842,595

(22) Filed: Apr. 26, 2001

(65) Prior Publication Data

US 2002/0061915 A1 May 23, 2002

Related U.S. Application Data

(63) Continuation-in-part of application No. 09/746,060, filed on Dec. 22, 2000, now Pat. No. 6,414,156, and a continuation-in-part of application No. 09/727,957, filed on Dec. 1, 2000, and a continuation-in-part of application No. 09/616,627, filed on Jul. 26, 2000, now abandoned.
(60) Provisional application No. 60/200,068, filed on Apr. 27, 2000.

(51) Int. Cl.$^7$ ............................................. A61K 31/425
(52) U.S. Cl. ....................... 514/369; 514/370; 514/371
(58) Field of Search ................................ 514/369, 370, 514/371

(56) References Cited

U.S. PATENT DOCUMENTS 6,214,852 B1 * 4/2001 Kimball ...................... 514/369

6,414,156 B2 * 7/2002 Chen ........................... 546/209

FOREIGN PATENT DOCUMENTS

WO 99/24416 5/1999

OTHER PUBLICATIONS

Database BIOSIS Abstract No. PREV200000198664 XP002181227, 91st Annual Meeting of the American Association for Cancer Research, San Francisco, CA, Apr. 1–5, 2000.

* cited by examiner

*Primary Examiner*—Robert Gerstl
(74) *Attorney, Agent, or Firm*—Rena Patel

(57) ABSTRACT

The invention provides a method for preventing or treating alopecia induced by chemotherapy or radiotherapy by administering to a mammalian specie in need thereof a therapeutically effective amount of a compound of formula I or II

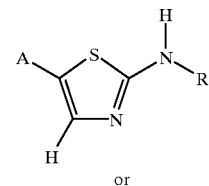

(I)

or

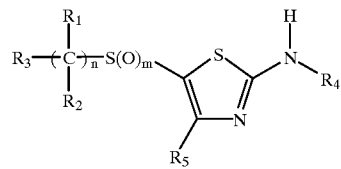

(II)

or a pharmaceutically acceptable salt thereof.

43 Claims, No Drawings

METHODS FOR PREVENTING AND TREATING ALOPECIA INDUCED BY CHEMOTHERAPY OR RADIOTHERAPY

This application is a continuation-in-part application of U.S. patent application Ser. No. 09/746,060, filed Dec. 22, 2000 now U.S. Pat. No. 6,414,156; Ser. No. 09/727,957, filed Dec. 1, 2000; Ser. No. 09/616,627, filed Jul. 26, 2000, now abandoned, all of these hereby incorporated by reference herein. This application claims priority to U.S. Provisional Application No. 60/200,068, filed Apr. 27, 2000, which is hereby incorporated by reference herein.

BACKGROUND OF THE INVENTION

Alopecia is a common and distressing side effect of many chemotherapeutic agents. In addition, alopecia also occurs as a side effect of radiotherapy. As patients embark on new therapies, hair loss can induce a negative body image, alter interpersonal relationships, and often cause patients to reject potentially curative therapy.

Several preventive methods have been proposed. Those methods include scalp tourniquet, scalp hypothermia, or a combination of both, the rationale of which is to reduce the blood circulation during chemotherapy or radiotherapy. However, none of those methods has been shown to have a definitive protective effect, although undesirable effects, such as headaches, may arise.

More recently, Jiminez et al. (WO 93/00079), Lishko et al. (U.S. Pat. No. 5,753,263), and Davis et al. (WO 99/15500) have disclosed methods for preventing and treating chemotherapy- and radiotherapy-induced alopecia. However, the active agents disclosed in those applications and patent are structurally distinct from the compounds of the present invention.

In spite of the research that has been done in the past, and further in view of the limited success of currently available chemotherapy-induced alopecia treatments, there is a long-felt yet unmet need in the art for an improved treatment for alopecia induced by chemotherapy and radiotherapy.

Accordingly, it is an object of the present invention to provide a new method for the treatment of alopecia induced by chemotherapy and radiotherapy.

BRIEF DESCRIPTION OF THE INVENTION

The present invention provides a method for preventing or treating alopecia induced by chemotherapy or radiotherapy which comprises administering to a mammalian specie in need thereof a therapeutically effective amount of a compound of formulas I or II

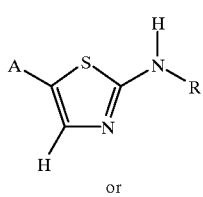

(I)

or

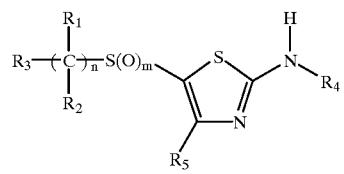

(II)

or enantiomers, diastereomers, solvates, and pharmaceutically acceptable salts thereof. As used in formulas I and II, and throughout the specification, the symbols have the following meanings:

R is $R_6$, $COR_7$, $CONH_2$, $CONR_6R_7$, $COOR_6$ or $SO_2R_6$;

$R_6$ is alkyl, cycloalkyl, heterocycloalkyl, cycloalkylalkyl, heterocycloalkylalkyl, aryl, heteroaryl, arylalkyl or heteroarylalkyl;

$R_7$ is H, alkyl, cycloalkyl, heterocycloalkyl, cycloalkylalkyl, heterocycloalkylalkyl, aryl, heteroaryl, arylalkyl or heteroarylalkyl;

A is 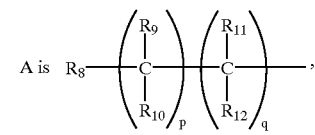

where p is 0, 1 or 2; and q is 1 or 2 but both p and q cannot be 2, or

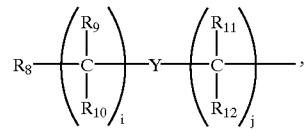

where i and j are each independently 0 or 1 but cannot both be 1, and Y is optionally substituted alkene, alkyne, or any 2 adjacent carbon atoms of a cycloalkyl or cycloheteroalkyl ring of 3–7 atoms;

$R_8$ is alkyl with two or more carbon atoms, cycloalkyl, heterocycloalkyl, cycloalkylalkyl, heterocycloalkylalkyl, aryl, heteroaryl, arylalkyl, heteroarylalkyl or $R_{13}$;

$R_9$, $R_{10}$, $R_{11}$ and $R_{12}$ are each independently H, alkyl, cycloalkyl, heterocycloalkyl, cycloalkylalkyl, heterocycloalkylalkyl, aryl, heteroaryl, arylalkyl, heteroarylalkyl, halo, or hydroxy, alkoxy, amino, $NR_{14}R_{15}$, thio or alkylthio, provided that only one hydroxy, alkoxy, amino, $NR_{14}R_{15}$, thio or alkylthio group is bonded to any one carbon atom;

$R_{13}$ is 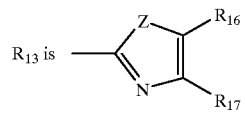

where Z is O, $NR_{18}$ or S;

$R_{16}$ and $R_{17}$ are each independently H, alkyl, cycloalkyl, heterocycloalkyl, cycloalkylalkyl, heterocycloalkylalkyl, aryl, heteroaryl, arylalkyl, heteroarylalkyl, halo, hydroxy, alkoxy, alkylcarbonyloxy, carboxy, alkyloxycarbonyl, amino, $NR_{19}R_{20}$, carbamoyl, ureido, thio or alkylthio;

$R_{14}$, $R_{15}$, $R_{18}$, $R_{19}$ and $R_{20}$ are each independently H, alkyl, cycloalkyl, heterocycloalkyl, cycloalkylalkyl, heterocycloalkylalkyl, aryl, heteroaryl, arylalkyl or heteroarylalkyl;

$R_1$ and $R_2$ are each independently hydrogen, fluorine or alkyl;

$R_3$ is aryl or heteroaryl;

$R_4$ is hydrogen, alkyl, cycloalkyl, aryl, cycloalkylalkyl, arylalkyl, heteroaryl, heteroarylalkyl, heterocycloalkyl, heterocycloalkylalkyl; or CO-alkyl, CO-cycloalkyl, CO-aryl, CO-alkyl-cycloalkyl, CO-alkyl-aryl, CO-heteroaryl, CO-alkyl-heteroaryl, CO-heterocycloalkyl, CO-alkyl-heterocycloalkyl; or CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or COO-alkyl, COO-cycloalkyl, COO-aryl, COO-alkyl-cycloalkyl, COO-alkyl-aryl, COO-heteroaryl, COO-alkyl-heteroaryl, COO-heterocycloalkyl, COO-alkyl-heterocycloalkyl; or $SO_2$-cycloalkyl, $SO_2$-aryl, $SO_2$-alkyl-cycloalkyl, $SO_2$-alkyl-aryl, $SO_2$-heteroaryl, $SO_2$-alkyl-heteroaryl, $SO_2$-heterocycloalkyl, $SO_2$-alkyl-heterocycloalkyl; or C(NCN)NH-alkyl, C(NCN)NH-cycloalkyl, C(NCN)NH-aryl, C(NCN)NH-alkyl-cycloalkyl, C(NCN)NH-alkyl-aryl, C(NCN)NH-heteroaryl, C(NCN)NH-alkyl-heteroaryl, C(NCN)NH-heterocycloalkyl, C(NCN)NH-alkyl-heterocycloalkyl; or $C(NNO_2)$NH-alkyl, $C(NNO_2)$NH-cycloalkyl, $C(NNO_2)$NH-aryl, $C(NNO_2)$NH-alkyl-cycloalkyl, $C(NNO_2)$NH-alkyl-aryl, $C(NNO_2)$NH-heteroaryl, $C(NNO_2)$NH-alkyl-heteroaryl, $C(NNO_2)$NH-heterocycloalkyl, $C(NNO_2)$NH-alkyl-heterocycloalkyl; or C(NH)NH-alkyl, C(NH)NH-cycloalkyl, C(NH)NH-aryl, C(NH)NH-alkyl-cycloalkyl, C(NH)NH-alkyl-aryl, C(NH)NH-heteroaryl, C(NH)NH-alkyl-heteroaryl, C(NH)NH-heterocycloalkyl, C(NH)NH-alkyl-heterocycloalkyl; or C(NH)NHCO-alkyl, C(NH)NHCO-cycloalkyl, C(NH)NHCO-aryl, C(NH)NHCO-alkyl-cycloalkyl, C(NH)NHCO-alkyl-aryl, C(NH)NHCO-heteroaryl, C(NH)NHCO-alkyl-heteroaryl, C(NH)NHCO-heterocycloalkyl, C(NH)NHCO-alkyl-heterocycloalkyl; or $C(NOR_{21})$NH-alkyl, $C(NOR_{21})$NH-cycloalkyl, $C(NOR_{21})$NH-aryl, $C(NOR_{21})$NH-alkyl-cycloalkyl, $C(NOR_{21})$NH-alkyl-aryl, $C(NOR_{21})$NH-heteroaryl, $C(NOR_{21})$NH-alkyl-heteroaryl, $C(NOR_{21})$NH-heterocycloalkyl, $C(NOR_{21})$NH-alkyl-heterocycloalkyl;

$R_5$ is hydrogen or alkyl;

$R_{21}$ is hydrogen, alkyl, cycloalkyl, aryl, cycloalkylalkyl, arylalkyl, heteroaryl, heteroarylalkyl, heterocycloalkyl or heterocycloalkylalkyl;

m is an integer of 0 to 2; and n is an integer of 1 to 3.

Advantageously, it has been found that the compounds of formulas I and II are useful for preventing or treating alopecia induced by chemotherapy or radiotherapy (radiation treatment).

DESCRIPTION OF THE INVENTION

The present invention provides methods for preventing and treating alopecia induced by chemotherapy or radiotherapy by administering to a mammalian specie, preferably a human, in need thereof a therapeutically effective amount of a compound of formula I or II.

The formula I compounds and methods for their preparation are described in WO 99/65884 and the formula II compounds and methods for their preparation are described in WO 99/24416, both of which are incorporated herein by reference thereto. Alternatively, compounds of formula II can be prepared by the processes discussed below.

Listed below are definitions of various terms used to describe the compounds of the instant invention. These definitions apply to the terms as they are used throughout the specification (unless they are otherwise limited in specific instances) either individually or as part of a larger group.

As used herein, the phrase "compounds of the invention" means, collectively, compounds falling within formulas I and II and pharmaceutically-acceptable salts, solvates, and hydrates thereof. Methods of salt formation, solvation, and hydrate formation are well known in the art. The invention also encompasses mixtures of stereoisomers of compounds of the invention. Stereoisomers include, but are not limited to, enantiomers, diastereomers, and racemates where the compound has one or more chiral centers. All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization. All configurational isomers of compounds of the present invention are contemplated, either in admixture or in pure or substantially pure form. The definition of compounds of the present invention very particularly embraces both cis (Z) and trans (E) alkene isomers, as well as cis and trans isomers of cycloalkyl or heterocycloalkyl rings.

In addition, salts of compounds of formulas I and II that are pharmaceutically unsuitable but useful in other respects, for example, for the isolation or purification of compounds of formulas I or II, are also encompassed by the invention.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The phrase "pharmaceutically-acceptable salt(s)," as used herein includes, but is not limited to, salts of acidic or basic groups that may be present in the compounds of the invention. Examples of such pharmaceutically acceptable salts include, but are not limited to, hydrochloride, hydrobromide, dihydrochloride, sulfate, trifluoroacetate, tartrate, fumarate, succinate, maleate, citrate, methanesulfonate, bromate and iodate salts and mixtures thereof. Also included are salts formed with other organic and inorganic acids such as hydroxymethane sulfonic acid, acetic acid, benzenesulfonic acid, toluenesulfonic acid and various others, e.g., nitrates, phosphates, borates, benzoates, ascorbates, salicylates, and the like. In addition, pharmaceutically acceptable salts of compounds of formula I can be formed with alkali metals, such as sodium, potassium and lithium; alkaline earth metals, such as calcium and magnesium; organic bases, such as dicyclohexylarnine, tributylamine, and pyridines, and the like; and amino acids, such as arginine, lysine, and the like.

Salts of compounds of the invention encompass solvates, racemates, and all stereoisomeric forms thereof, including enantiomers and diastereomers (for example, D-tartrate and L-tartrate salts).

As used herein, the term "solvate" means a compound of the invention or a salt thereof, that further includes a stoichiometric or non-stoichiometric amount of a solvent bound by non-covalent intermolecular forces. Preferred solvents are volatile, non-toxic, and/or acceptable for administration to humans in trace amounts. When the solvent is water the solvate is termed a "hydrate".

It should be noted that any heteroatom with unsatisfied valances is assumed to have the hydrogen atoms necessary to satisfy the valances.

Carboxylate anion refers to a negatively charged group —COO$^-$.

The term "alkyl" or "alk" refers to a monovalent alkane (hydrocarbon) derived radical containing from 1 to 12 carbon atoms unless otherwise defined. An alkyl group is an optionally substituted straight, branched or cyclic saturated hydrocarbon group. When substituted, alkyl groups may be substituted with up to four substituent groups, $R_{22}$ as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary $R^{22}$ substituents may include, but are not limited to, one or more of the following groups: halo (such as F, Cl, Br or I), haloalkyl (such as $CCl_3$ or $CF_3$), alkoxy, alkylthio, hydroxy, carboxy (—COOH), alkyloxycarbonyl, alkylcarbonyloxy, amino (—$NH_2$), carbamoyl, urea, amidinyl or thiol (—SH). Alkyl groups as defined may also comprise one or more carbon to carbon double bonds or one or more carbon to carbon triple bonds.

The term "alkenyl" refers to a hydrocarbon radical straight, branched or cyclic containing from 2 to 12 carbon atoms and at least one carbon to carbon double bond.

The term "alkynyl" refers to a hydrocarbon radical straight, branched or cyclic containing from 2 to 12 carbon atoms and at least one carbon to carbon triple bond.

Cycloalkyl is a specie of alkyl containing from 3 to 15 carbon atoms, without alternating or resonating double bonds between carbon atoms. It may contain from 1 to 4 rings. Exemplary unsubstituted such groups include cyclopropyl, cyclobutyl, cyclopentyl, cyclohexyl, adamantyl, etc. Exemplary substituents include one or more of the following groups: halogen, alkyl, alkoxy, alkyl hydroxy, amino, nitro, cyano, thiol and/or alkylthio.

The terms "alkoxy" or "alkylthio", as used herein, denote an alkyl group as described above bonded through an oxygen linkage (—O—) or a sulfur linkage (—S—), respectively.

Sulfoxide and sulfone denote groups bonded by —SO— and —$SO_2$— linkages respectively.

The term "alkoxycarbonyl", as used herein, denotes an alkoxy group bonded through a carbonyl group.

The term "alkylcarbonyl" refers to an alkyl group bonded through a carbonyl group.

The term "alkylcarbonyloxy", as used herein, denotes an alkycarbonyl group that is bonded through an oxygen linkage.

The term "arylalkyl", as used herein, denotes an aromatic ring bonded to an alkyl group as described above.

The term "aryl" refers to monocyclic or bicyclic aromatic rings, e.g., phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to, halogen, alkyl, alkoxy, hydroxy, carboxy, carbamoyl, alkyloxycarbonyl, nitro, trifluoromethyl, amino, cycloalkyl, cyano, alkyl $S(O)_t$ (t=0, 1 or 2) or thiol.

The term "heteroaryl" refers to a monocyclic aromatic hydrocarbon group having 5 or 6 ring atoms, or a bicyclic aromatic group having 8 to 10 atoms, containing at least one heteroatom, O, S, or N, in which a carbon or nitrogen atom is the point of attachment, and in which one or two additional carbon atoms is optionally replaced by a heteroatom selected from O or S, and in which 1 to 3 additional carbon atoms are optionally replaced by nitrogen heteroatoms, said heteroaryl group being optionally substituted as described herein. Exemplary heteroaryl groups include the folowing: thienyl, furyl, pyrrolyl, pyridyl, imidazolyl, pyrrolidinyl, piperidinyl, thiazolyl, oxazolyl, triazolyl, pyrazolyl, isoxazolyl, isothiazolyl, pyrazinyl, tetrazolyl, pynrdazinyl, pyrimidinyl, triazinylazepinyl, indolyl, isoindolyl, quinolinyl, isoquinolinyl, benzothiazolyl, benzoxazolyl, benzimidazolyl, benzoxadiazolyl, benzofurazanyl and tetrahydropyranyl. Exemplary substituents include one or more of the following: halogen, alkyl, alkoxy, hydroxy, carboxy, carbamoyl, alkyloxycarbonyl, trifluoromethyl, cycloalkyl, nitro, cyano, amino, alkyl$S(O)_t$ (t=0, 1 or 2) or thiol.

The term "heteroarylium" refers to heteroaryl groups bearing a quaternary nitrogen atom and thus a positive charge.

The term "heterocycloalkyl" refers to a cycloalkyl group (nonaromatic) in which one of the carbon atoms in the ring is replaced by a heteroatom selected from O, S or N, and in which up to three additional carbon atoms may be replaced by said heteroatoms.

The term "quaternary nitrogen" refers to a tetravalent positively charged nitrogen atom including, e.g., the possitively charged nitrogen in a tetraalkylammonium group (e.g., tetramethylammonium, N-methylpyridinium), the positively charged nitrogen in protonated ammonium species (e.g., trimethylhydroammonium, N-hydropyridinium), the positively charged nitrogen in amine N-oxides (e.g., N-methyl-morpholine-N-oxide, pyridine-N-oxide), and the positively charged nitrogen in an N-amino-ammonium group (e.g., N-aminopyridinium).

The term "heteroatom" means O, S or N, selected on an independent basis.

The term "halogen" or "halo" refers to chlorine, bromine, fluorine or iodine.

Preferred formula I compounds are those wherein

R is $R_6$, $COR_7$ or $CONR_6R_7$;

$R_6$ is alkyl, aryl, heteroaryl, arylalkyl or heteroarylalkyl;

$R_7$ is H, alkyl, aryl, heteroaryl, arylalkyl or heteroarylalkyl;

A is 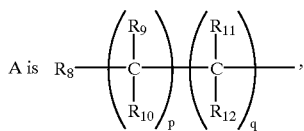

where p is 0, 1 or 2; and q is 1 or 2, or

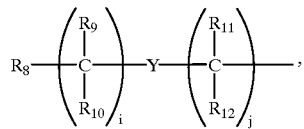

where i and j are each independently 0 or 1 but cannot both be 1, and Y is optionally substituted alkene, alkyne, or any two adjacent carbon atoms of a cycloalkyl ring;

$R_8$ is alkyl with two or more carbon atoms, aryl, heteroaryl or $R_{13}$;

$R_9$, $R_{10}$, $R_{11}$ and $R_{12}$ are each independently H or alkyl;

$R_{13}$ is 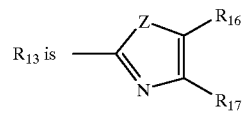

where Z is O; and $R_{16}$ and $R_{17}$ are each independently H, alkyl or cycloalkyl.

More preferred formula I compounds are those wherein

R is $COR_7$;

$R_7$ is H, alkyl, heteroaryl, arylalkyl or heteroarylalkyl;

A is 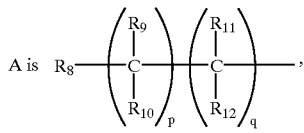

where p is 0 or 1; and q is 1, or

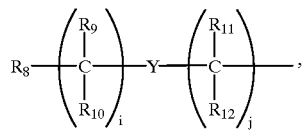

where i and j are each independently 0 or 1 but cannot both be 1, and Y is an optionally substituted alkene;

$R_8$ is $R_{13}$;

$R_9$, $R_{10}$, $R_{11}$ and $R_{12}$ are each independently H or alkyl;

$R_{13}$ is 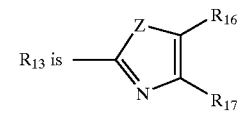

where Z is O; and $R_{16}$ and $R_{17}$ are each independently H, alkyl or cycloalkyl.

A second group of more preferred compounds of formula I are those wherein

R is $COR_7$;

$R_7$ is alkyl, arylalkyl, heteroaryl or heteroarylalkyl;

A is 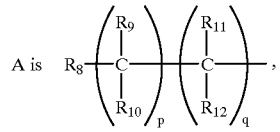

where p is 0 or 1; and q is 1;

$R_9$, $R_{10}$, $R_{11}$ and $R_{12}$ are each independently H or alkyl;

$R_8$ is $R_{13}$;

$R_{13}$ is 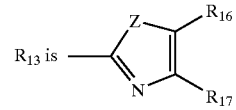

where Z is O;

$R_{16}$ is alkyl or cycloalkyl; and $R_{17}$ is H.

A third group of more preferred compounds of formula I are those wherein

R is $COR_7$;

$R_7$ is alkyl, arylalkyl, heteroaryl or heteroarylalkyl;

A is 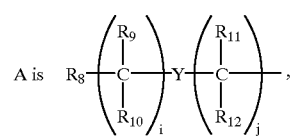

where i and j are each independently 0 or 1 but cannot both be 1, and Y is an optionally substituted alkene or alkyne;

$R_8$ is $R_{13}$;

$R_9$, $R_{10}$, $R_{11}$ and $R_{12}$ are each independently H or alkyl;

$R_{13}$ is 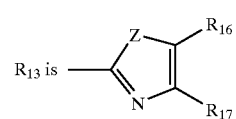

where Z is O;

$R_{16}$ is alkyl or cycloalkyl; and $R_{17}$ is H.

A fourth group of more preferred compounds of formula I are those wherein

R is $R_6$;

$R_6$ is alkyl, aryl, heteroaryl, arylalkyl or heteroarylalkyl;

A is 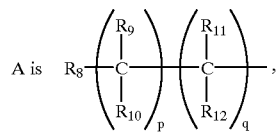

where p is 0 or 1; and q is 1,or

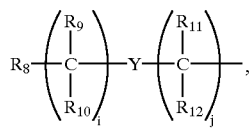

where i and j are each independently 0 or 1 but cannot both be 1, and Y is an optionally substituted alkene;

$R_8$ is $R_{13}$;

$R_9$, $R_{10}$, $R_{11}$ and $R_{12}$ are each independently H or alkyl;

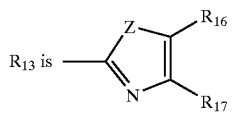

where Z is O; and $R_{16}$ and $R_{17}$ are each independently H, alkyl or cycloalkyl.

A fifth group of more preferred formula I compounds are those wherein

R is $R_6$;

$R_6$ is alkyl, aryl, heteroaryl, arylalkyl or heteroarylalkyl;

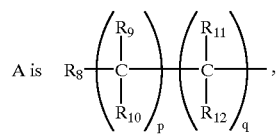

where p is 0 or 1; and q is 1;

$R_9$, $R_{10}$, $R_{11}$ and $R_{12}$ are each independently H or alkyl;

$R_8$ is $R_{13}$;

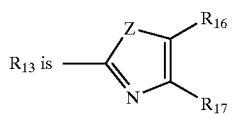

where Z is O;

$R_{16}$ is alkyl or cycloalkyl; and $R_{17}$ is H.

A sixth group of more preferred compounds of formula I are those wherein

R is $R_6$;

$R_6$ is alkyl, aryl, arylalkyl, heteroaryl or heteroarylalkyl;

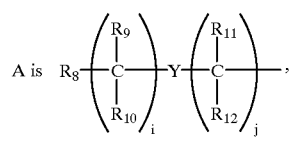

where i and j are each independently 0 or 1 but cannot both be 1, and Y is an optionally substituted alkene or alkyne;

$R_8$ is $R_{13}$;

$R_9$, $R_{10}$, $R_{11}$ and $R_{12}$ are each independently H or alkyl;

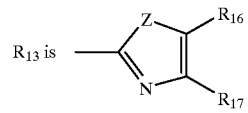

where Z is O;

$R_{16}$ is alkyl or cycloalkyl; and $R_{17}$ is H.

A seventh group of more preferred formula I compounds are those wherein

R is $CONR_6R_7$;

$R_6$ is alkyl, heteroaryl, arylalkyl or heteroarylalkyl;

$R_7$ is H, alkyl, heteroaryl, arylalkyl or heteroarylalkyl;

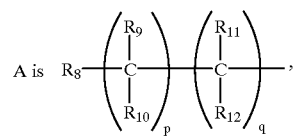

where p is 0 or 1; and q is 1, or

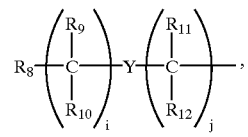

where i and j are each independently 0 or 1 but cannot both be 1, and Y is an optionally substituted alkene;

$R_8$ is $R_{13}$;

$R_9$, $R_{10}$, $R_{11}$ and $R_{12}$ are each independently H or alkyl;

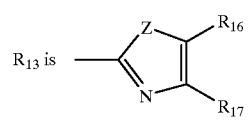

where Z is O; and $R_{16}$ and $R_{17}$ are each independently H, alkyl or cycloalkyl.

An eighth group of more preferred compounds of formula I are those wherein

R is $CONR_6R_7$;

$R_6$ is alkyl, arylalkyl, heteroaryl or heteroarylalkyl;

$R_7$ is H, alkyl, heteroaryl, arylalkyl or heteroarylalkyl;

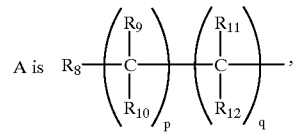

where p is 0 or 1; and q is 1;

$R_8$ is $R_{13}$;
$R_9$, $R_{10}$, $R_{11}$ and $R_{12}$ are each independently H or alkyl;

$R_{13}$ is 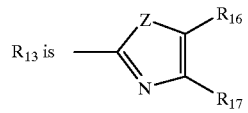

where Z is O;
$R_{16}$ is alkyl or cycloalkyl; and
$R_{17}$ is H.

A ninth group of more preferred compounds of formnula I are those wherein
R is $CONR_6R_7$;
$R_6$ is alkyl, arylalkyl, heteroaryl or heteroarylalkyl;
$R_7$ is H, alkyl, heteroaryl, arylky or hetroarylalkyl;

A is 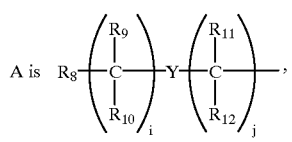

where i and j are each independently 0 or 1 but cannot both be 1, and Y is an optionally substituted alkene or alkyne;
$R_8$ is $R_{13}$;
$R_9$, $R_{10}$, $R_{11}$ and $R_{12}$ are each independently H or alkyl;

$R_{13}$ is 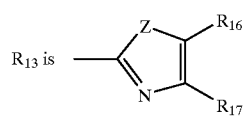

where Z is O;
$R_{16}$ is alkyl or cycloalkyl; and
$R_{17}$ is H.

Preferred compounds of formula II (designated herein as Group IIa) are those wherein
$R_1$ and $R_2$ are each independently hydrogen or alkyl;

$R_3$ is 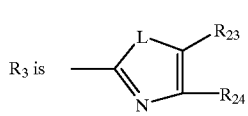

where L is oxygen, sulfur or $NR_{25}$;
$R_4$ is hydrogen, alkyl, cycloalkyl, aryl, cycloalkylalkyl, arylalkyl, heteroaryl, heteroarylalkyl, heterocycloalkyl, heterocycloalkylalkyl; or
  CO-alkyl, CO-cycloalkyl, CO-aryl, CO-alkyl-cycloalkyl, CO-alkyl-aryl, CO-heteroaryl, CO-alkyl-heteroaryl, CO-heterocycloalkyl, CO-alkyl-heterocycloalkyl; or
  CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or
  COO-alkyl, COO-cycloalkyl, COO-aryl, COO-alkyl-cycloalkyl, COO-alkyl-aryl, COO-heteroaryl, COO-alkyl-heteroaryl, COO-heterocycloalkyl, COO-alkyl-heterocycloalkyl; or
  $SO_2$-cycloalkyl, $SO_2$-aryl, $SO_2$-alkyl-cycloalkyl, $SO_2$-alkyl-aryl, $SO_2$-heteroaryl, $SO_2$-alkyl-heteroaryl, $SO_2$-heterocycloalkyl, $SO_2$-alkyl-heterocycloalkyl; or C(NCN)NH-alkyl, C(NCN)NH-cycloalkyl, C(NCN)NH-aryl, C(NCN)NH-alkyl-cycloalkyl, C(NCN)NH-alkyl-aryl, C(NCN)NH-heteroaryl, C(NCN)NH-alkyl-heteroaryl, C(NCN)NH-heterocycloalkyl, C(NCN)NH-alkyl-heterocycloalkyl; or $C(NNO_2)$NH-alkyl, $C(NNO_2)$NH-cycloalkyl, $C(NNO_2)$NH-aryl, $C(NNO_2)$NH-alkyl-cycloalkyl, $C(NNO_2)$NH-alkyl-aryl, $C(NNO_2)$NH-heteroaryl, $C(NNO_2)$NH-alkyl-heteroaryl, $C(NNO_2)$NH-heterocycloalkyl, $C(NNO_2)$NH-alkyl-heterocycloalkyl; or C(NH)NH-alkyl, C(NH)NH-cycloalkyl, C(NH)NH-aryl, C(NH)NH-alkyl-cycloalkyl, C(NH)NH-alkyl-aryl, C(NH)NH-heteroaryl, C(NH)NH-alkyl-heteroaryl, C(NH)NH-heterocycloalkyl, C(NH)NH-alkyl-heterocycloalkyl; or C(NH)NHCO-alkyl, C(NH)NHCO-cycloalkyl, C(NH)NHCO-aryl, C(NH)NHCO-alkyl-cycloalkyl, C(NH)NHCO-alkyl-aryl, C(NH)NHCO-heteroaryl, C(NH)NHCO-alkyl-heteroaryl, C(NH)NHCO-heterocycloalkyl, C(NH)NHCO-alkyl-heterocycloalkyl; or $C(NOR_{21})$NH-alkyl, $C(NOR_{21})$NH-cycloalkyl, $C(NOR_{21})$NH-aryl, $C(NOR_{21})$NH-alkyl-cycloalkyl, $C(NOR_{21})$NH-alkyl-aryl, $C(NOR_{21})$NH-heteroaryl, $C(NOR_{21})$NH-alkyl-heteroaryl, $C(NOR_{21})$NH-heterocycloalkyl, $C(NOR_{21})$NH-alkyl-heterocycloalkyl;

$R_5$ is hydrogen or alkyl;

$R_{21}$ is hydrogen, alkyl, cycloalkyl, aryl, cycloalkylalkyl, arylalkyl, heteroaryl, heteroarylalkyl, heterocycloalkyl or heterocycloalkylalkyl;

$R_{23}$ and $R_{24}$ are each independently hydrogen, alkyl, substituted alkyl, cycloalkyl, aryl, substituted aryl, cycloalkylalkyl, arylalkyl, heteroaryl, substituted heteroaryl, heteroarylalkyl, heterocycloalkyl or heterocycloalkylalkyl;

$R_{25}$ is hydrogen, alkyl, cycloalkyl, aryl, alkylcycloalkyl, arylalkyl, heteroaryl, heteroarylalkyl, heterocycloalkyl or heterocycloalkylalkyl;

m is an integer of 0 to 2; and n is an integer of 1 to 3.

More preferred compounds of formula II (designated herein as Group IIb) are those wherein
$R_1$ and $R_2$ are each independently hydrogen or alkyl;

$R_3$ is 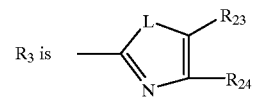

where L is oxygen;
$R_4$ is hydrogen, alkyl, cycloalkyl, aryl, cycloalkylalkyl, arylalkyl, heteroaryl, heteroarylalkyl, heterocycloalkyl, heterocycloalkylalkyl; or
  CO-alkyl, CO-cycloalkyl, CO-aryl, CO-alkyl-cycloalkyl, CO-alkyl-aryl, CO-heteroaryl, CO-alkyl-heteroaryl, CO-heterocycloalkyl, CO-alkyl-heterocycloalkyl; or
  CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or
  COO-alkyl, COO-cycloalkyl, COO-aryl, COO-alkyl-cycloalkyl, COO-alkyl-aryl, COO-heteroaryl, COOalkyl-heteroaryl, COO-heterocycloalkyl, COO-alkyl-heterocycloalkyl; or SO$_2$-cycloalkyl, SO$_2$-aryl, SO$_2$-alkyl-cycloalkyl, SO$_2$-alkyl-aryl, SO$_2$-heteroaryl, SO$_2$-alkyl-heteroaryl, SO$_2$-heterocycloalkyl, SO$_2$-alkyl-heterocycloalkyl; or C(NCN)NH-alkyl, C(NCN)NH-cycloalkyl, C(NCN)NH-aryl, C(NCN)NH-alkyl-cycloalkyl, C(NCN)NH-alkyl-aryl, C(NCN)NH-heteroaryl, C(NCN)NH-alkyl-heteroaryl, C(NCN)NH-heterocycloalkyl, C(NCN)NH-alkyl-heterocycloalkyl; or C(NNO$_2$)NH-alkyl, C(NNO$_2$)NH-cycloalkyl, C(NNO$_2$)NH-aryl, C(NNO$_2$)NH-alkyl-cycloalkyl, C(NNO$_2$)NH-alkyl-aryl, C(NNO$_2$)NH-heteroaryl, C(NNO$_2$)NH-alkyl-heteroaryl, C(NNO$_2$)NH-heterocycloalkyl, C(NNO$_2$)NH-alkyl-heterocycloalkyl; or C(NH)NH-alkyl, C(NH)NH-cycloalkyl, C(NH)NH-aryl, C(NH)NH-alkyl-cycloalkyl, C(NH)NH-alkyl-aryl, C(NH)NH-heteroaryl, C(NH)NH-alkyl-heteroaryl, C(NH)NH-heterocycloalkyl, C(NH)NH-alkyl-heterocycloalkyl; or C(NH)NHCO-alkyl, C(NH)NHCO-cycloalkyl, C(NH)NHCO-aryl, C(NH)NHCO-alkyl-cycloalkyl, C(NH)NHCO-alkyl-aryl, C(NH)NHCO-heteroaryl, C(NH)NHCO-alkyl-heteroaryl, C(NH)NHCO-heterocycloalkyl, C(NH)NHCO-alkyl-heterocycloalkyl; or C(NOR$_{21}$)NH-alkyl, C(NOR$_{21}$)NH-cycloalkyl, C(NOR$_{21}$)NH-aryl, C(NOR$_{21}$)NH-alkyl-cycloalkyl, C(NOR$_{21}$)NH-alkyl-aryl, C(NOR$_{21}$)NH-heteroaryl, C(NOR$_{21}$)NH-alkyl-heteroaryl, C(NOR$_{21}$)NH-heterocycloalkyl, C(NOR$_{21}$)NH-alkyl-heterocycloalkyl;

R$_5$ is hydrogen;

R$_{21}$ is hydrogen, alkyl, cycloalkyl, aryl, cycloalkylalkyl, arylalkyl, heteroaryl, heteroarylalkyl, heterocycloalkyl or heterocycloalkylalkyl;

R$_{23}$ and R$_{24}$ are each independently hydrogen, alkyl, substituted alkyl, cycloalkyl, aryl, substituted aryl, cycloalkylalkyl, arylalkyl, heteroaryl, substituted heteroaryl, heteroarylalkyl, heterocycloalkyl or heterocycloalkylalkyl;

m is an integer of 0 to 2; and n is an integer of 1 to 3.

A second group of more preferred formula II compounds (designated herein as Group IIc) are those wherein R$_1$ and R$_2$ are each independently hydrogen or alkyl;

R$_3$ is 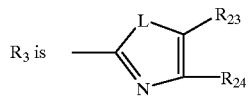

where L is sulfur;

R$_4$ is hydrogen, alkyl, cycloalkyl, aryl, cycloalkylalkyl, arylalkyl, heteroaryl, heteroarylalkyl, heterocycloalkyl, heterocycloalkylalkyl; or CO-alkyl, CO-cycloalkyl, CO-aryl, CO-alkyl-cycloalkyl, CO-alkyl-aryl, CO-heteroaryl, CO-alkyl-heteroaryl, CO-heterocycloalkyl, CO-alkyl-heterocycloalkyl; or CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or COO-alkyl, COO-cycloalkyl, COO-aryl, COO-alkyl-cycloalkyl, COO-alkyl-aryl, COO-heteroaryl, COO-alkyl-heteroaryl, COO-heterocycloalkyl, COO-alkyl-heterocycloalkyl; or SO$_2$-cycloalkyl, SO$_2$-aryl, SO$_2$-alkyl-cycloalkyl, SO$_2$-alkyl-aryl, SO$_2$-heteroaryl, SO$_2$-alkyl-heteroaryl, SO$_2$-heterocycloalkyl, SO$_2$-alkyl-heterocycloalkyl; or C(NCN)NH-alkyl, C(NCN)NH-cycloalkyl, C(NCN)NH-aryl, C(NCN)NH-alkyl-cycloalkyl, C(NCN)NH-alkyl-aryl, C(NCN)NH-heteroaryl, C(NCN)NH-alkyl-heteroaryl, C(NCN)NH-heterocycloalkyl, C(NCN)NH-alkyl-heterocycloalkyl; or C(NNO$_2$)NH-alkyl, C(NNO$_2$)NH-cycloalkyl, C(NNO$_2$)NH-aryl, C(NNO$_2$)NH-alkyl-cycloalkyl, C(NNO$_2$)NH-alkyl-aryl, C(NNO$_2$)NH-heteroaryl, C(NNO$_2$)NH-alkyl-heteroaryl, C(NNO$_2$)NH-heterocycloalkyl, C(NNO$_2$)NH-alkyl-heterocycloalkyl; or C(NH)NH-alkyl, C(NH)NH-cycloalkyl, C(NH)NH-aryl, C(NH)NH-alkyl-cycloalkyl, C(NH)NH-alkyl-aryl, C(NH)NH-heteroaryl, C(NH)NH-alkyl-heteroaryl, C(NH)NH-heterocycloalkyl, C(NH)NH-alkyl-heterocycloalkyl; or C(NH)NHCO-alkyl, C(NH)NHCO-cycloalkyl, C(NH)NHCO-aryl, C(NH)NHCO-alkyl-cycloalkyl, C(NH)NHCO-alkyl-aryl, C(NH)NHCO-heteroaryl, C(NH)NHCO-alkyl-heteroaryl, C(NH)NHCO-heterocycloalkyl, C(NH)NHCO-alkyl-heterocycloalkyl; or C(NOR$_{21}$)NH-alkyl, C(NOR$_{21}$)NH-cycloalkyl, C(NOR$_{21}$)NH-aryl, C(NOR$_{21}$)NH-alkyl-cycloalkyl, C(NOR$_{21}$)NH-alkyl-aryl, C(NOR$_{21}$)NH-heteroaryl, C(NOR$_{21}$)NH-alkyl-heteroaryl, C(NOR$_{21}$)NH-heterocycloalkyl, C(NOR$_{21}$)NH-alkyl-heterocycloalkyl;

R$_5$ is hydrogen;

R$_{21}$ is hydrogen, alkyl, cycloalkyl, aryl, cycloalkylalkyl, arylalkyl, heteroaryl, heteroarylalkyl, heterocycloalkyl or heterocycloalkylalkyl;

R$_{23}$ and R$_{24}$ are each independently hydrogen, alkyl, substituted alkyl, cycloalkyl, aryl, substituted aryl, cycloalkylalkyl, arylalkyl, heteroaryl, substituted heteroaryl, heteroarylalkyl, heterocycloalkyl or heterocycloalkylalkyl;

m is an integer of 0 to 2; and n is an integer of 1 to 3.

A third group of more preferred compounds of formula II (designated herein as Group IId) are those wherein R$_1$ and R$_2$ are each independently hydrogen or alkyl;

R$_3$ is 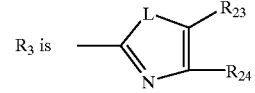

where L is NR$_{25}$;

R$_4$ is hydrogen, alkyl, cycloalkyl, aryl, cycloalkylalkyl, arylalkyl, heteroaryl, heteroarylalkyl, heterocycloalkyl, heterocycloalkylalkyl; or CO-alkyl, CO-cycloalkyl, CO-aryl, CO-alkyl-cycloalkyl, CO-alkyl-aryl, CO-heteroaryl, CO-alkyl-heteroaryl, CO-heterocycloalkyl, CO-alkyl-heterocycloalkyl; or CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or COO-alkyl, COO-cycloalkyl, COO-aryl, COO-alkyl-cycloalkyl, COO-alkyl-aryl, COO-heteroaryl, COO-alkyl-heteroaryl, COO-heterocycloalkyl, COO-alkyl-heterocycloalkyl; or $SO_2$-cycloalkyl, $SO_2$-aryl, $SO_2$-alkyl-cycloalkyl, $SO_2$-alkyl-aryl, $SO_2$-heteroaryl, $SO_2$-alkyl-heteroaryl, $SO_2$-heterocycloalkyl, $SO_2$-alkyl-heterocycloalkyl; or C(NCN)NH-alkyl, C(NCN)NH-cycloalkyl, C(NCN)NH-aryl, C(NCN)NH-alkyl-cycloalkyl, C(NCN)NH-alkyl-aryl, C(NCN)NH-heteroaryl, C(NCN)NH-alkyl-heteroaryl, C(NCN)NH-heterocycloalkyl, C(NCN)NH-alkyl-heterocycloalkyl; or $C(NNO_2)$NH-alkyl, $C(NNO_2)$NH-cycloalkyl, $C(NNO_2)$NH-aryl, $C(NNO_2)$NH-alkyl-cycloalkyl, $C(NNO_2)$NH-alkyl-aryl, $C(NNO_2)$NH-heteroaryl, $C(NNO_2)$NH-alkyl-heteroaryl, $C(NNO_2)$NH-heterocycloalkyl, $C(NNO_2)$NH-alkyl-heterocycloalkyl; or C(NH)NH-alkyl, C(NH)NH-cycloalkyl, C(NH)NH-aryl, C(NH)NH-alkyl-cycloalkyl, C(NH)NH-alkyl-aryl, C(NH)NH-heteroaryl, C(NH)NH-alkyl-heteroaryl, C(NH)NH-heterocycloalkyl, C(NH)NH-alkyl-heterocycloalkyl; or C(NH)NHCO-alkyl, C(NH)NHCO-cycloalkyl, C(NH)NHCO-aryl, C(NH)NHCO-alkyl-cycloalkyl, C(NH)NHCO-alkyl-aryl, C(NH)NHCO-heteroaryl, C(NH)NHCO-alkyl-heteroaryl, C(NH)NHCO-heterocycloalkyl, C(NH)NHCO-alkyl-heterocycloalkyl; or $C(NOR_{21})$NH-alkyl, $C(NOR_{21})$NH-cycloalkyl, $C(NOR_{21})$NH-aryl, $C(NOR_{21})$NH-alkyl-cycloalkyl, $C(NOR_{21})$NH-alkyl-aryl, $C(NOR_{21})$NH-heteroaryl, $C(NOR_{21})$NH-alkyl-heteroaryl, $C(NOR_{21})$NH-heterocycloalkyl, $C(NOR_{21})$NH-alkyl-heterocycloalkyl;

$R_5$ is hydrogen;

$R_{21}$ is hydrogen, alkyl, cycloalkyl, aryl, cycloalkylalkyl, arylalkyl, heteroaryl, heteroarylalkyl, heterocycloalkyl or heterocycloalkylalkyl;

$R_{23}$ and $R_{24}$ are each independently hydrogen, alkyl, substituted alkyl, cycloalkyl, aryl, substituted aryl, cycloalkylalkyl, arylalkyl, heteroaryl, substituted heteroaryl, heteroarylalkyl, heterocycloalkyl or heterocycloalkylalkyl;

$R_{25}$ is hydrogen, alkyl, cycloalkyl, aryl, cycloalkylalkyl, arylalkyl, heteroaryl, heteroarylalkyl, heterocycloalkyl or heterocycloalkylalkyl;

m is an integer of 0 to 2; and n is an integer of 1 to 3.

A fourth group of more preferred formula II compounds (designated herein as Group IIe) are those wherein $R_1$ and $R_2$ are each independently hydrogen or alkyl;

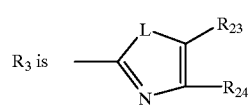

where L is oxygen;

$R_4$ is aryl, heteroaryl, CO-alkyl, CO-alkyl-aryl, CO-cycloalkyl, CO-alkyl-heteroaryl, CO-alkyl-heteroalkyl, CO-alkyl-heterocycloalkyl, CONH-alkyl, CONH-alkyl-aryl, CONH-cycloalkyl or CONH-alkyl-heterocycloalkyl;

$R_5$ is hydrogen;

$R_{23}$ and $R_{24}$ are hydrogen;

m is the integer 0; and n is the integer 1.

A fifth group of more preferred formula II compounds (designated herein as Group IIf) are those wherein $R_1$ and $R_2$ are independently hydrogen or alkyl;

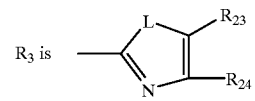

where L is oxygen;

$R_4$ is aryl, heteroaryl, CO-alkyl, CO-alkyl-aryl, CO-alkyl-heteroalkyl, CO-cycloalkyl, CO-alkyl-heterocycloalkyl, CO-alkyl-heteroaryl, CONH-alkyl, CONH-alkyl-aryl, CONH-cycloalkyl or CONH-alkyl-heterocycloalkyl;

$R_5$ is hydrogen;

$R_{23}$ is alkyl;

$R_{24}$ is hydrogen;

m is the integer 0; and n is the integer 1.

A sixth group of more preferred formula II compounds (designated herein as Group IIg) are those wherein $R_1$ and $R_2$ are independently hydrogen or alkyl;

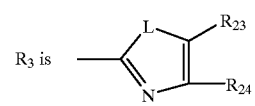

where L is sulfur;

$R_4$ is aryl, heteroaryl, CO-alkyl, CO-alkyl-aryl, CO-alkyl-heteroalkyl, CO-cycloalkyl, CO-alkyl-heterocycloalkyl, CO-alkyl-heteroaryl, CONH-alkyl, CONH-alkyl-aryl, CONH-cycloalkyl or CONH-alkyl-heterocycloalkyl;

$R_5$ is hydrogen;

$R_{23}$ is alkyl;

$R_{24}$ is hydrogen;

m is the integer 0; and n is the integer 1.

A seventh group of more preferred compounds of formula II (designated herein as Group IIh) are those wherein $R_1$ and $R_2$ are independently hydrogen or alkyl;

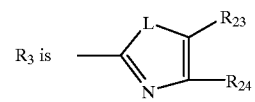

where L is $NR_{25}$;

$R_4$ is aryl, heteroaryl, CO-alkyl, CO-alkyl-aryl, CO-alkyl-heteroalkyl, CO-cycloalkyl, CO-alkyl-heterocycloalkyl, CO-alkyl-heteroaryl, CONH-alkyl, CONH-alkyl-aryl, CONH-cycloalkyl or CONH-alkyl-heterocycloalkyl;

$R_5$ is hydrogen;

$R_{23}$ is alkyl;

$R_{24}$ is hydrogen;

$R_{25}$ is hydrogen, alkyl, cycloalkyl, aryl, alkyl-cycloalkyl, alkyl-aryl, heteroaryl, alkyl-heteroaryl, heterocycloalkyl or alkyl-heterocycloalkyl;

m is the integer 0; and n is the integer 1.

An eighth group of more preferred compounds of formula II (designated herein as Group IIi) are those wherein $R_1$ and $R_2$ are independently hydrogen or alkyl;

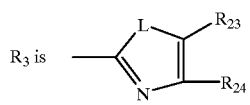

where L is $NR_{25}$;

$R_4$ is aryl, heteroaryl, CO-alkyl, CO-alkyl-aryl, CO-cycloalkyl, CO-alkyl-heteroaryl, CO-alkyl-heteroalkyl, CO-alkyl-heterocycloalkyl, CONH-alkyl, CONH-alkyl-aryl, CONH-cycloalkyl or CONH-alkyl-heterocycloalkyl;

$R_5$ is hydrogen;

$R_{23}$ is hydrogen;

$R_{24}$ is alkyl;

$R_{25}$ is hydrogen;

m is the integer 0; and n is the integer 1.

An ninth group of more preferred compounds of formula II (designated herein as Group IIj) are compounds of the formula:

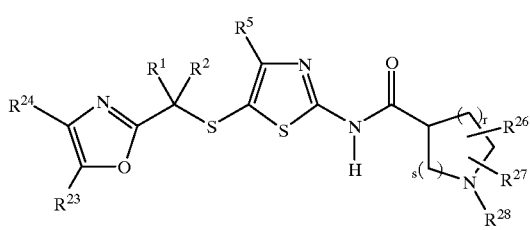

or enantiomers, diastereomers, solvates, and pharmaceutically acceptable salts thereof, wherein:

$R^1$, $R^2$, and $R^5$ are independently hydrogen or alkyl;

$R^{23}$ is alkyl, aryl, or heteroaryl;

$R^{24}$ is hydrogen, alkyl, aryl, or heteroaryl;

$R^{26}$ and $R^{27}$ are independently hydrogen, alkyl, aryl, heteroaryl, halogen, hydroxy, or alkoxy;

$R^{28}$ is hydrogen, alkyl, cycloalkyl, aryl, heteroaryl, $CONR^{29}R^{30}$, $COR^{31}$, or $COOR^{32}$;

$R^{29}$, $R^{30}$, $R^{31}$ and $R^{32}$ are independently hydrogen, alkyl, or aryl;

r is an integer ranging from 0 to 5; and s is an integer ranging from 0 to 5.

A tenth group of more preferred compounds of formula II (designated herein as Group IIk) are compounds of the formula:

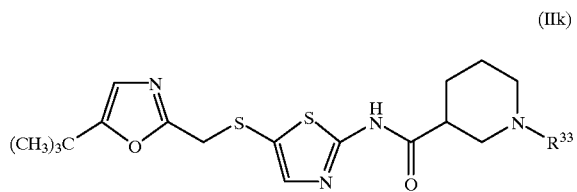

and enantiomers, diastereomers, solvates, and pharmaceutically acceptable salts thereof, wherein $R^{33}$ is hydrogen, alkyl, or cycloalkyl.

An eleventh group of more preferred compounds of formula II (designated herein as Group III) are compounds of the formula:

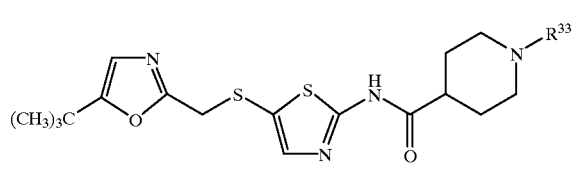

and enantiomers, diastereomers, solvates, and pharmaceutically acceptable salts thereof, wherein $R^{33}$ is hydrogen, alkyl, or cycloalkyl.

A twelfth group of more preferred compounds of formula II (designated herein as Group IIm) are compounds of the formula:

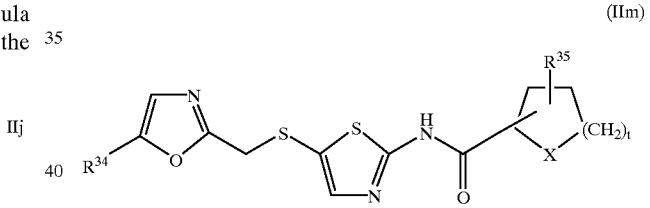

and enantiomers, diastereomers, solvates, and pharmaceutically acceptable salts thereof, wherein:

$R^{34}$ is alkyl;

$R^{35}$ is hydrogen or alkyl;

X is $NR^{36}$ or $CHNR^{36}R^{37}$;

$R^{36}$ and $R^{37}$ are independently hydrogen, alkyl, or cycloalkyl; and t is 0, 1, 2 or 3.

A thirteenth group of more preferred compounds of formula II (designated herein as Group IIn) are compounds of the formula:

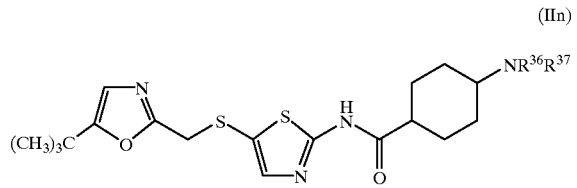

and enantiomers, diastereomers, solvates, and pharmaceutically acceptable salts thereof, wherein $R^{36}$ and $R^{37}$ are independently hydrogen, alkyl, or cycloalkyl.

In another embodiment, compounds of formula II include, but are not limited to, those listed in Table 1 below and enantiomers, diastereomers, solvates, and pharmaceutically acceptable salts thereof.

TABLE 1

Compounds of the Invention

| Name | Structure |
|---|---|
| N-[5-[[[5-(1,1-dimethylethyl)-2-oxazolyl]methyl]thio]-2-thiazolyl]-4-piperidinecarboxamide | 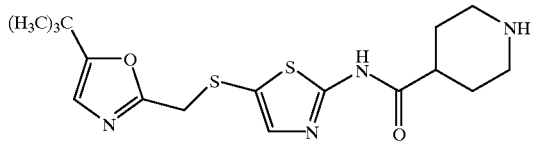 |
| (±)-N-[5-[[[5-(1,1-dimethylethyl)-2-oxazolyl]methyl]thio]-2-thiazolyl]-3-piperidinecarboxamide | 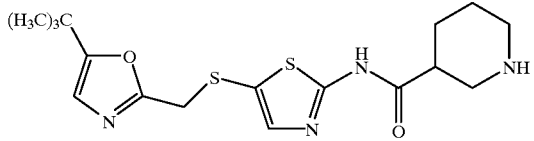 |
| (±)-1-(2,3-dihydroxypropyl)-N-[5-[[[5-(1,1-dimethylethyl)-2-oxazolyl]methyl]thio]-2-thiazolyl]-4-piperidinecarboxamide | 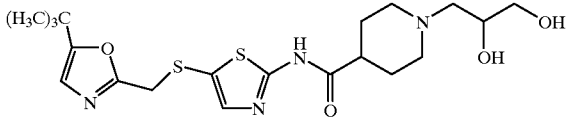 |
| N-[5-[[[5-(1,1-dimethylethyl)-2-oxazolyl]methyl]thio]-2-thiazolyl]-1-(1-methylethyl)-4-piperidinecarboxamide | 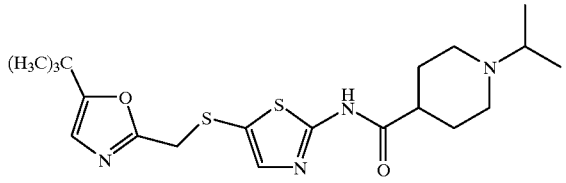 |
| 1-cyclopropyl-N-[5-[[[5-(1,1-dimethylethyl)-2-oxazolyl]methyl]thio]-2-thiazolyl]-4-piperidinecarboxamide | 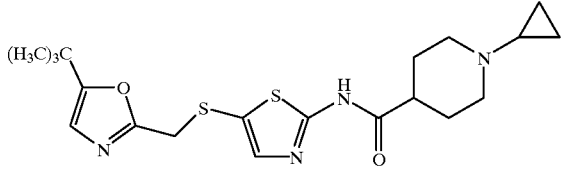 |
| N-[5-[[[5-(1,1-dimethylethyl)-2-oxazolyl]methyl]thio]-2-thiazolyl]-1-(2-hydroxyethyl)-4-piperidinecarboxamide | 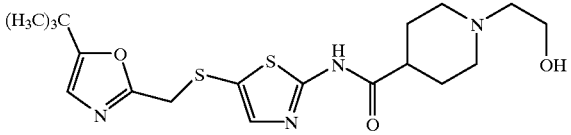 |
| (R)-N-[5-[[[5-(1,1-dimethylethyl)-2-oxazolyl]methyl]thio]-2-thiazolyl]-3-piperidinecarboxamide | 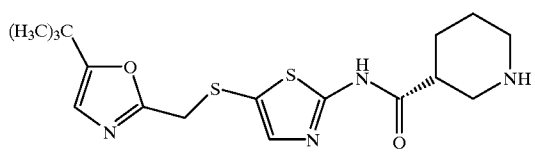 |
| (S)-N-[5-[[[5-(1,1-dimethylethyl)-2-oxazolyl]methyl]thio]-2-thiazolyl]-3-piperidinecarboxamide | 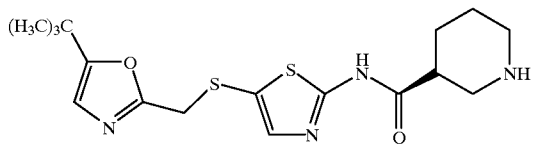 |

TABLE 1-continued

Compounds of the Invention

| Name | Structure |
|---|---|
| cis-4-amino-N-[5-[[[5-(1,1-dimethylethyl)-2-oxazolyl]methyl]thio]-2-thiazolyl]cyclohexylycarboxamide | |
| trans-4-amino-N-[5-[[[5-(1,1-dimethylethyl)-2-oxazolyl]methyl]thio]-2-thiazolyl]cyclohexylcarboxamide | 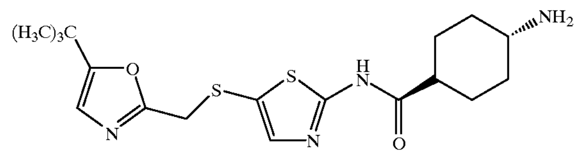 |

Preferred salts of the above compounds are the hydrochloride, the hydrobromide, the dihydrochloride, the sulfate, the trifluoroacetate, the tartrate, the fumarate, the succinate, the maleate, the citrate, the methanesulfonate, the bromate, and the iodate salts or mixtures thereof.

In addition to the methods described in WO 99/24416 and WO 99/65884, certain compounds of the invention, such as those of formula IIj, can be prepared as described in Scheme 1 below. Thus, in another embodiment, the present invention relates to processes for the synthesis of compounds of the formula IIj:

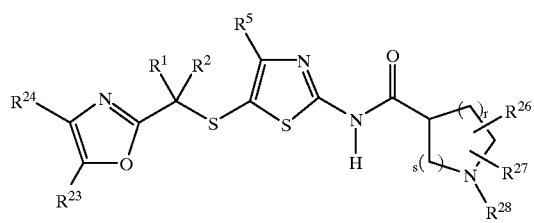

IIj wherein:

$R^1$, $R^2$, and $R^5$ are independently hydrogen or alkyl;

$R^{23}$ is alkyl, aryl, or heteroaryl;

$R^{24}$ is hydrogen, alkyl, aryl, or heteroaryl;

$R^{26}$ and $R^{27}$ are independently hydrogen, alkyl, aryl, heteroaryl, halogen, hydroxy, or alkoxy;

$R^{28}$ is hydrogen, alkyl, cycloalkyl, aryl, heteroaryl, $CONR^{29}R^{30}$, $COR^{31}$, or $COOR^{32}$;

$R^{29}$, $R^{30}$, $R^{31}$ and $R^{32}$ are independently hydrogen, alkyl, or aryl;

r is an integer ranging from 0 to 5; and s is an integer ranging from 0 to 5.

This method is preferred for the synthesis of compounds of the formula IIj but can be adapted by those of skill in the art for the synthesis of other compounds of the invention. The synthetic reactions of this embodiment are outlined below in Scheme 1, where the following terms apply:

L is a suitable leaving group, such as halogen or sulfonate ($R^{25}SO_2O^-$, $CF_3SO_2O^-$, etc., wherein $R^{25}$ is alkyl, cycloalkyl, or aryl);

M is hydrogen, Li, Na, K, Cs, or a quaternary ammonium ion, e.g., $(R^{25})_4N$ or quaternary ammonium ions comprising cyclic alkenetetramines, such as hexamethylenetetramine;

X is hydroxy, halogen or acyloxy ($R^{25}COO^-$, $R^{25}OCOO^-$, etc.);

Y is O, S, NH, N-alkyl, N-aryl or N-acyl;

Z is hydrogen, alkyl, aryl, O-alkyl, O-aryl, S-alkyl, S-aryl, $NH_2$, N-alkyl, N-aryl or N-acyl; and P is a nitrogen-protecting group (Boc, Cbz, $R_3Si$, etc.). When a functional group is termed "protected," this means that the group is in modified form to preclude undesired side reactions at the protected site. Suitable protecting groups for the compounds involved in the present processes will be recognized from the specification taking into account the level of skill in the art, and with reference to standard textbooks such as Greene, T. W., *Protective Groups in Organic Synthesis,* 3rd edition (1999), incorporated herein by reference.

The processes generally involve reaction of α-halo ketones 2 (commercially available or readily synthesized by well-known methods) with an azide to give α-azido ketones 3. Reduction of 3 with a reducing reagent gives α-amino ketones 4.

Alternatively and more advantageously, the α-amino ketones 4 are prepared by reaction of α-halo ketones 2 with a cyclic alkylenetetramine such as hexamethylenetetramine and the like, followed by hydrolysis of the resulting, new quaternary ammonium salt 3'. This reaction provides excellent yields of the desired intermediate compound 4, above 90%.

Thereafter, reacting the α-amino ketones 4 with an α-halo acyl halide 5 in the presence of a base or, alternatively, coupling the α-amino ketones 4 with an α-halo acid, produces the corresponding amides 6. Then, ring closure of 6 with a dehydrating reagent affords 2-oxazolylalkyl halides 7. When a conventional dehydrating reagent, such as trihalophosphorus oxide like $POCl_3$, is used, product isolation is difficult due to the formation of large amounts of hydrochloric and phosphoric acids. Thus, the process of the present invention preferably utilizes the Burgess' reagent which produces excellent yields and permits easy, safe product isolation from water.

Subsequent treatment of 2-oxazolylalkyl halides 7 with sulfur-containing reagent 8 or 8' affords new key intermediate compounds, 2-oxazolylalkyl sulfides 9. Coupling of 9 with 5-halo-2-aminothiazole 10 gives 5-(2-oxazolylalkylthio)-2-aminothiazoles 11. Coupling of 11 with an azacycloalkanoic acid derivative 12 affords thiazolyl amides 13, which may be deprotected (in the case where P is a protecting group, e.g., Boc) to give 5-(2-oxazolylalkylthio)-2-azacycloalkanoylaminothiazoles II.

While specifically described for synthesis of compounds of formula IIj, the synthetic methods outlined in Scheme 1, or appropriate steps thereof, can be adapted or used directly by one of skill in the art for the synthesis of other compounds of general formulas I and II.

Scheme 1

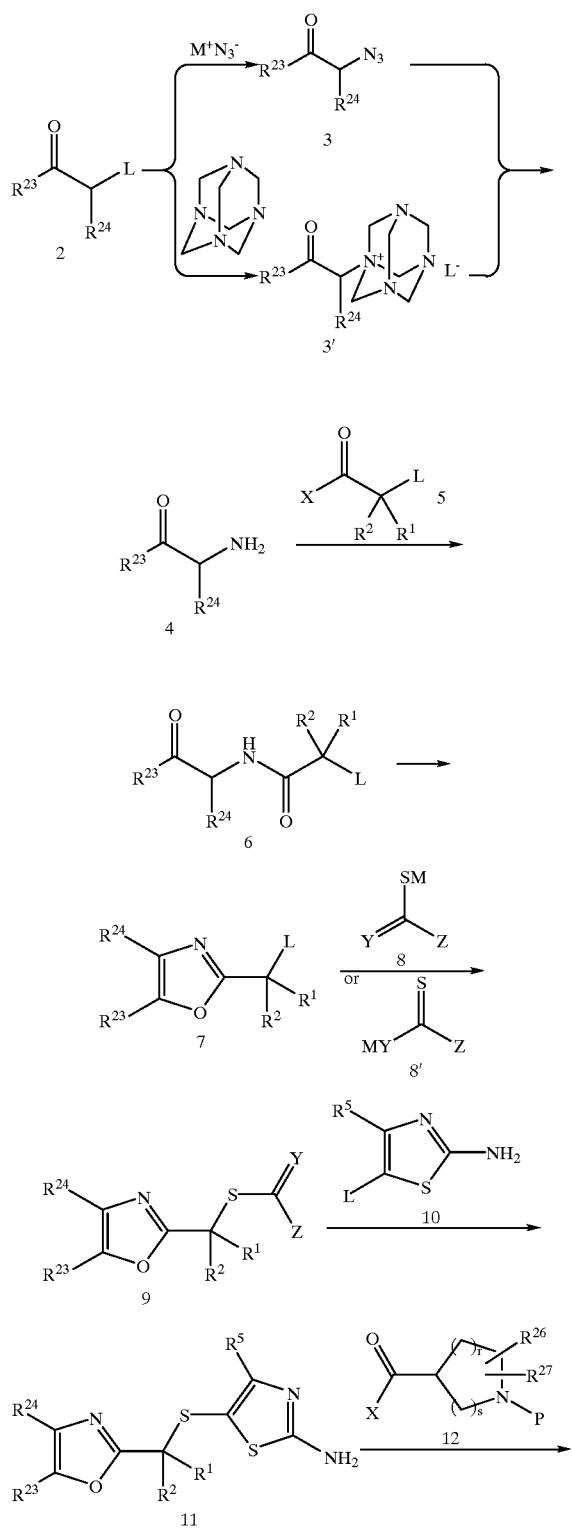

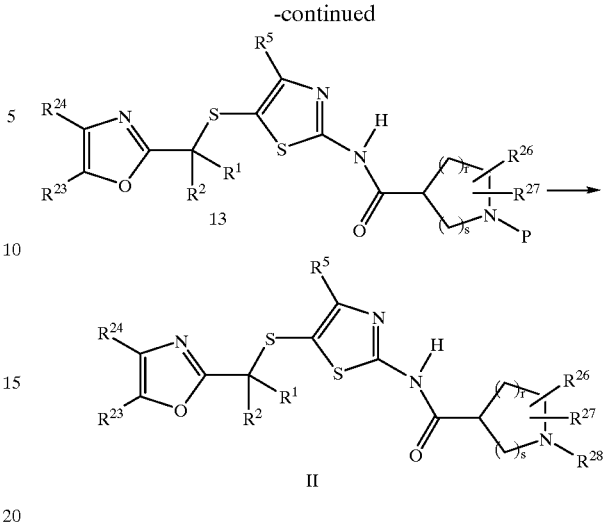

As set forth in Scheme 1, the processes for the preparation of 5-(2-oxazolylalkylthio)-2-azacycloalkanoylaminothiazoles and analogs involve the following transformations:

Step (a) involves reacting an a-substituted ketone 2 such as, for example, an α-halo ketone, with an azide in a suitable solvent or solvent mixtures to give an α-azido ketone 3; or, more desirably, (a') reacting an a-substituted ketone 2 like the α-halo ketone with a cyclic alkylenetetramine such as, for example, hexamethylenetetramine in a suitable solvent or solvent mixtures to give a new quaternary ammonium salt 3'.

The α-halo ketone includes α-halo aliphatic and α-halo aromatic ketones. The preferred α-halo ketones are α-halo pinacolones with α-bromo pinacolone most preferred. A sulfonate, for example, $RSO_2O$— (where R is alkyl, aryl or heteroaryl), $CF_3SO_2O$— and the like, may be substituted for the halogen in the α-position. The azides include both metal azides and quaternary ammonium azides. The metal azides are preferred with sodium azide most preferred. Suitable solvent(s) include solvents such as hydrocarbons, ethers, amides, for example, dimethylformamide, ketones, etc., or mixtures thereof, with ketones such as acetone preferred for both reactions (a) and (a').

Step (b) comprises reacting the α-azido ketone 3 obtained in step (a) with a reducing reagent in a suitable solvent or solvent mixtures to give an α-amino ketone 4, or, more desirably, (b') reacting the quaternary ammonium salt 3' obtained in step (a') with an acid in a suitable solvent or solvent mixtures to give an α-amino ketone 4.

The reducing reagent in reaction (b) includes hydrogen in the presence of a transition metal catalyst such as palladium, trialkyl or triarylphosphines like triphenylphosphine. Hydrogen in the presence of a transition metal catalyst is preferred with hydrogen and palladium over activated carbon most preferred. Suitable solvent(s) in reaction (b) include solvents such as hydrocarbons, ethers, alcohols and the like, or mixtures thereof, with alcohol such as methanol preferred. Alternatively, the reduction reaction can be carried out in the presence of an acidic medium such as, for example, hydrochloric acid in ethanol to give α-amino ketone acid salt which can be isolated as the acid salt or free amine forms.

The acid in reaction (b') includes, but is not limited to, protic acids such as HCl, HBr, HI, $H_2SO_4$, $H_3PO_4$, etc., with HCl preferred. Suitable solvent(s) in reaction (b') include solvents such as hydrocarbons, ethers, alcohols and the like, or mixtures thereof, with alcohol such as ethanol preferred. The α-amino ketone product may be isolated as the salt or free base forms.

Step (c) involves reacting (acylating) the α-amino ketone 4 or its acid salt obtained in step (b) or (b') with an a-substituted acyl derivative 5 such as, for example, an α-halo acyl halide, in the presence of a base and in a suitable solvent or solvent mixtures to give an amide 6.

The α-halo acyl halide 5 includes α-alkyl or aryl substituted or unsubstituted α-halo acyl halide with the latter preferred. The most preferred α-halo acyl halide is α-chloroacetyl chloride. The base used in the reaction includes, but is not limited to, aromatic and aliphatic organic amines with the latter preferred. The most preferred base is triethylamine. Suitable solvent(s) include aprotic solvents such as hydrocarbons, halogenated hydrocarbons, ethers, esters and the like, or mixtures thereof, with halogenated hydrocarbons such as dichloromethane preferred. Alternatively, the reaction can be carried out using an α-substituted acid instead of the α-substituted acyl derivative and then employing a coupling reagent such as a water-soluble diimide like carbodiimide, haloformate, thionyl halide, etc. In either reaction, a sulfonate, for example, $RSO_2O—$ (where R is an alkyl, aryl or heteroaryl), $CF_3SO_2O—$ and the like, may be substituted for the halogen in the α-position of the α-halo acyl halide or the α-halo acid reactants which are illustrated.

Step (d) concerns reacting the amide 6 obtained in step (c) with a dehydrating reagent in a suitable solvent or solvent mixtures to give the cyclized 2-oxazolylalkyl derivative 7 such as, for example, the 2-oxazolylalkyl halide.

Advantageously, the reaction is carried out using (methoxycarbonylsulfamoyl)-triethylammonium hydroxide (Burgess' reagent) as the dehydrating reagent. Suitable solvent(s) include hydrocarbons, halogenated hydrocarbons, ethers and the like, or mixtures thereof. Most preferred is the use of the Burgess' reagent in tetrahydrofuran. Suitable dehydrating reagents also include, but are not limited to, other bases, acids, acid anhydrides and the like, such as, e.g., concentrated sulfuric acid, polyphosphoric acid, etc. Although less conveniently, the dehydrating reagent, for instance, can be trihalophosphorus oxide such as tribromophosphorus oxide or trichlorophosphorus oxide, alone or with a solvent like toluene.

Step (e) is directed to reacting the 2-oxazolylalkyl derivative 7 obtained in step (d) with a sulfur-containing reagent 8 or 8' in a suitable solvent or solvent mixtures to give 2-oxazolylalkyl sulfide 9, a new key intermediate compound.

The sulfur-containing reagent includes N-substituted or unsubstituted thioureas, thio acids or salts such as thioacetic acid or its salt, xanthic acids or salts such as ethylxanthic acid potassium salt. Unsubstituted thiourea is preferred. Suitable solvent(s) include hydrocarbons, halogenated hydrocarbons, ethers, esters, amides, alcohols and the like, or mixtures thereof, with alcohol such as methanol or ethanol preferred.

Step (f) concerns reacting the 2-oxazolylalkyl sulfide 9 obtained in step (e) with a 5-halo-2-aminothiazole 10 in the presence of a base and in a suitable solvent or solvent mixtures to give 5-(2-oxazolylalkylthio)-2-aminothiazole 11.

The 5-halo-2-aminothiazole includes 4-N-substituted or unsubstituted 5-halo-2-aminothiazoles with 5-bromo-2-aminothiazole preferred. A suitable base includes, but is not limited to, metal hydroxide, metal alkoxides, metal carbonates and aqueous amines such as ammonium hydroxide. Sodium hydroxide is preferred. Suitable solvent(s) include solvents such as hydrocarbons, halogenated hydrocarbons, ethers, esters, amides, alcohols and the like, or mixtures thereof, with halogenated hydrocarbons such as dichloromethane preferred.

Step (g) involves reacting the 5-(2-oxazolylalkylthio)-2-aminothiazole 11 obtained in step (f) with an azacycloalkanoic acid derivative 12 in the presence of a coupling reagent in a suitable solvent or solvent mixtures to give thiazolyl amide 13.

The azacycloalkanoic acid derivative includes N-protected derivatives, for example, N-protected isonipecotic acid or N-protected nip ecotic acid. The preferred nitrogen-protecting groups are Boc, Cbz, silicon derivatives and the like with Boc being the most preferred. The coupling reagent includes, but is not limited to, water-soluble carbodiimides, haloformates and the like, with carbodiimides such as alkylcarbodiimides being preferred. Suitable solvent(s) include solvents such as hydrocarbons, halogenated hydrocarbons, ethers, esters, amides, etc., or mixtures thereof, with halogenated hydrocarbons such as dichloromethane preferred.

Step (h) is directed to reacting the thiazolyl amide 13 obtained in step (g) with a deprotecting reagent in a suitable solvent or solvent mixtures to give a desired 5-(2-oxazolylalkylthio)-2-azacycloalkanoylaminothiazole II (where $R^{27}$ is hydrogen).

The choice of the deprotecting reagent is based on the nature of the protecting group (P). For the Boc protecting group, the preferred deprotecting reagent is an acid such as hydrochloric acid or trifluoroacetic acid and suitable solvent (s) for such deprotecting reaction include solvents such as hydrocarbons, halogenated hydrocarbons, ethers, esters, amides and the like, or mixtures thereof, with halogenated hydrocarbons such as dichloromethane preferred.

The starting compounds of Scheme 1 are commercially available or may be prepared by methods known to one of ordinary skill in the art.

To further illustrate Scheme 1, a process to make 5-(5-t-butyl-2-oxazolylmethylthio)-2-azacycloalkanoylaminothiazoles and analogs thereof, for example, starts with reaction of α-bromo pinacolone 2 ($R_{23}$=Bu-t, $R^{24}$=H, L=Br) with sodium azide to give an α-azido pinacolone 3 ($R^{23}$=Bu-t, $R^{24}$=H). Reduction of α-azido pinacolone 3 ($R^{23}$=Bu-t, $R^{24}$=H) with a reducing reagent gives α-amino pinacolone 4 ($R^{23}$=Bu-t, $R^{24}$=H). Alternatively and more desirably, the α-amino pinacolone 4 ($R^{23}$=Bu-t, $R^{24}$=H) is prepared by reaction of α-bromo pinacolone 2 ($R^{23}$=Bu-t, $R^{24}$=H, L=Br) with hexamethylenetetramine followed by hydrolysis of the resulting quaternary ammonium salt 3'($R^{23}$=Bu-t, $R^{24}$=H, L=Br). Coupling of α-amino pinacolone 4 ($R^{23}$=Bu-t, $R^{24}$=H) with an α-chloroacetyl chloride 5 ($R^2$=$R^1$=H, L=X=Cl) produces amide 6 ($R^{23}$=Bu-t, $R^{24}$=$R^2$=$R^1$=H, L=Cl). Ring closure of 6 with a dehydrating reagent affords 5-t-butyl-2-oxazolylmethyl chloride 7 ($R^{23}$=Bu-t, $R^{24}$=$R^2$=$R^1$=H, L=Cl). Treatment of 7 with sulfur-containing reagent 8 or 8' such as thiourea affords 5-t-butyl-2-oxazolylalkyl sulfide 9 ($R^{23}$=Bu-t, $R^{24}$=$R^2$=$R^1$=H, Y=NH, Z=$NH_2$). Coupling of 9 with 5-bromo-2-aminothiazole 10 ($R^5$=H, L=Br) gives 5-(5-t-butyl-2-oxazolylmethylthio)-2-aminothiazole 11 ($R^{23}$=Bu-t, $R^{24}$=$R^2$=$R^1$=$R^5$=H). Coupling of 11 with N-Boc azacycloalkanoic acid 12 (X=OH, $R^{26}$=$R^{27}$=H, r=0, s=2, P=Boc), affords thiazolyl amide 13 ($R^{23}$=Bu-t, $R^{24}$=$R^2$=$R^1$=$R^5$=$R^{26}$=$R^{27}$=H, r=0, s=2, P=Boc), which after deprotection, gives rise to the desired 5-(5-t-butyl-2-oxazolylmethylthio)-2-azacycloalkanoylaminothiazole II ($R^{23}$=Bu-t, $R^{24}$=$R^2$=$R^1$=$R^5$=$R^{26}$=$R^{27}$=$R^{28}$=H, r=0, s=2).

The present invention provides a method for preventing or treating chemotherapy-induced alopecia in a mammal, prior to, during, or after undergoing chemotherapy by administering to the mammal with a therapeutically effective amount of a compound of formula I or II. The present invention also provides a method for preventing or treating radiotherapy-induced alopecia in a mammal prior to, during, or after undergoing radiotherapy by administering to the mammal with a therapeutically effective amount of a compound of formula I or II. The therapeutically effective amount of the formula I or II compound is that amount sufficient to prevent or reduce the hair loss that normally accompanies chemotherapy or radiotherapy treatments.

The compounds of this invention may be administered in topical, oral, nasal, ophthalmic, otic, rectal, intravenous, intraperitoneal, intraarticular, subcutaneous, intramuscular, inhalation or insufflation form, all using forms well known to those of ordinary skill in the pharmaceutical arts. In a preferred embodiment of the present invention, the compounds are topically administered to the skin, preferably the scalp of a patient.

The dosage regimen utilizing the compounds of the present invention is selected in accordance with a variety of factors including type, species, age, weight, sex and medical condition of the patient; the amount of chemotherapeutic agent(s) or radiotherapy administered or planned to be administered to the patient; the route of administration; and the particular compound or salt thereof employed. An ordinarily skilled physician or veterinarian can readily determine and prescribe the effective amount of the drug required to prevent, counter or arrest the chemotherapy or radiotherapy-induced alopecia.

Topical application is the preferred administration route. Topical application may be once or more than once per day depending upon the usual medical considerations. Topical administration, preferably to the scalp, 1 to 2 times prior to chemotherapy or radiotherapy administration would be preferred to prevent alopecia, additional applications may be administered as needed. The compounds of the present invention may be administered in a single daily dose, or the total daily dosage may be administered in divided doses of two, three or four times daily before, during, or after the chemotherapy or radio therapy. The compounds of this invention may be prepared in a range of concentrations for topical use. In general, topical compositions comprise about 0.1 mg to 25 mg of active compound per ml of suitable carrier.

In the methods of the present invention, the compounds of formulas I and II are the active ingredient, and are typically administered in admixture with suitable pharmaceutical diluents, excipients or carriers (collectively referred to herein as "carrier" materials) suitably selected with respect to the intended form of administration, that is, topical creams, lotions, solutions, dispersions, shampoos, ointments, gels, spot-ons, dusts, aerosols and the like; and oral tablets, capsules, elixirs, syrups and the like; and consistent with conventional pharmaceutical practices.

The compounds of this invention may also be administered in the form of liposome delivery systems, such as small unilamellar vesicles, large unilamellar vesicles and multilamellar vesicles. Liposomes can be formed from a variety of phospholipids such as cholesterol, stearylamine or phosphatidylcholines. Liposomal compositions and methods for their preparation are well known to those skilled in the pharmaceutical arts.

The present invention also relates to pharmaceutical compositions containing a compound of formula I or II in combination with a pharmaceutically acceptable carrier to prevent or treat chemotherapy or radiotherapy-induced alopecia. Topical formulations suitable for use in the methods of the present invention include, but are not limited to, creams, lotions, solutions, dispersions, shampoos, ointments, gels, spot-ons, dusts, impregnated dressings, aerosols, and the like. The topical formulations may contain appropriate conventional additives such as preservatives, solvents, coloring agents, emollients, and the like.

Keratinocyte Proliferation Assay

Death of proliferating stem cells in the hair follicles has a dramatic impact on the retention of hair following chemotherapy/radiotherapy treatment. The activity of the compounds of this invention to inhibit stem cell proliferation and protect them from chemotherapy/radiotherapy-induced cell death may be evaluated in a keratinocyte proliferation assay using the following procedure.

Adult female mice are shaved on the dorsal skin beginning on day 1. Hyperplasia is induced by treatment with the phorbol ester TPA (5 µg topically in 0.2 ml acetone) the morning of the next day (day 2), and is called time zero (T-0). At time points relative to that treatment, inhibitors are added to prevent the induced proliferation of keratinocytes. For twice a day dosing, drugs are typically administered 30 minutes after TPA (T-0.5) and again eight hours later (T-8). On day 3, at T-23, mice are injected with BrdU (4.5 mg in 0.3 ml PBS). One hour later (T-24) mice are euthanized, and the skin removed for preparation of keratinocytes.

First, subdermal fat is removed by scraping with a scalpel, the skin is washed with DPBS, and allowed to dry for ~10 minutes in a cell culture dish. Keratinocytes are liberated from the tissue by the addition of 10 ml of 0.25% trypsin/EDTA, and tissue maceration with scissors. Subsequent incubation at 37° C. in 5% $CO_2$ for 2–3 hours completes the dissociation of cells from the dermis.

Digested skin tissue is pipetted through a Falcon 2350 cell strainer into centrifuge tubes. Recovery of keratinocytes is enriched by rinsing the cell strainer with 10 ml keratinocyte media (KM: S-MEM/10% dialyzed FBS supplemented with Insulin, EGF, Transferrin, phosphoethanolamine, ethanolamine, hydrocortisone, and glutamine). The cells are concentrated by centrifugation and resuspended in 10 ml fresh KM.

Basal keratinocytes are separated from other cell types by centrifugation through a gradient by layering the suspended cell pellet on top of 20 ml of 45% Percoll (w/1.5 mM NaCl) and centrifugation at 1000 RPM in a refrigerated clinical centrifuge (4° C.). The cell pellet is resuspended in 80% EtOH, and placed at −20° C. overnight.

The next day, about 2 million cells are removed from the ethanol solution and prepared for flow cytometry analysis by centrifugation and resuspension in 1 ml of 2N HCl (in 0.5% Triton X-100). The cells are incubated in this solution for 30 minutes, with intermittent mixing. The cells are removed from this solution by centrifugation, and washed with 1.0 ml of 0.1M sodium tetraborate (pH 8.5), pelleted again, and resuspended in 1.0 ml 0.5% Tween 20 in 1% BSA. Conditioned cells are then pelleted and resuspended in 20 µl of antiBrdU antibody and incubated for 30 min. at room temperature. This immunoreaction is stopped by addition of 500 µl Tween20/BSA/BS solution, mixing and pelleting of the cells by centrifugation. Cells are counterstained by resuspending the cell pellet in 1.0 ml of 0.1 µM Topro-3 dye solution (100 μl of 10 mg/ml Rnase stock added to 10 ml PBS, plus 1 μl Topro-3 dye). Incubate 15 minutes. BrdU incorporation is scored by flow cytometry and a proliferative index is calculated. Test compounds which show a low proliferation index in this assay, as compared to high levels of proliferation induced by TPA alone, are predicted to protect hair follicles from chemotherapy/radiotherapy-induced alopecia.

In order to facilitate a further understanding of the invention, the following examples are presented primarily for the purpose of illustrating more specific details thereof. The scope of the invention should not be deemed limited by the examples, but encompasses the entire subject matter defined in the claims.

EXAMPLE 1
Preparation of 5-[5-(t-Butyl)-2-oxazolylmethylthio]-2-(azacycloalkanoylamino-thiazole hydrochloride

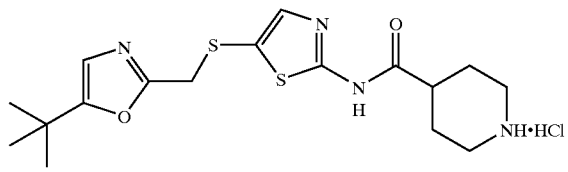

A. Preparation of α-Azido-pinacolone

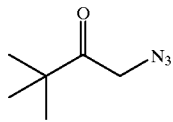

α-Bromo-pinacolone (199.07 g, 1.1115 mol, 1 eq) was combined in 1.785 L of acetone with sodium azide (93.9 g, 1.4444 mol, 1.3 eq). The reaction was stirred at room temperature for 27.5 hours. The resulting slurry was filtered and washed with acetone (3×150 mL). The filtrate was concentrated in vacuo to provide 154.3 g (98.4%) of the title compound. HPLC 83.85% at 2.57 minutes (Phenomenex Inc., Torrance, Calif., 5 μm C18 column 4.6×50 mm, 10–90% aqueous methanol over 4 minutes containing 0.2% phosphoric acid, 4 mL/min, monitoring at 220 nm).

B. Preparation of α-Hexamethylenetetramino-pinacolone Bromide

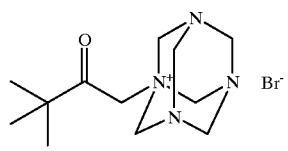

α-Bromo-pinacolone (179 g, 1 mol, 1 eq) was combined in 2 L of acetone with hexamethylenetetramine (154.21 g, 1.1 mol, 1.1 eq) and the reaction stirred under $N_2$ at room temperature for 26 hours. The resulting slurry was filtered, the filter cake was washed with ether (3×50 mL) and dried in vacuo at 50° C. overnight to provide 330 g (100%) of the title compound containing 7% hexamethylenetetramine. HPLC R.T.=0.17 min (Phenomenex Inc., 5 μm C18 column 4.6×50 mm, 10–90% aqueous methanol over 4 minutes containing 0.2% phosphoric acid, 4 mL/min, monitoring at 220 nm).

C. Preparation of α-Amino-pinacolone Hydrochloride

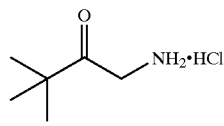

α-Azido-pinacolone (128.5 g, 0.911 mol) was combined in 4.2 L of methanol with 77.1 mL of concentrated HCl and 15.42 g of 10% Pd/C. The reaction mixture was stirred under hydrogen for 1.5 hours. The catalyst was removed by filtration. The solvent was distilled to give a wet solid. The residual water was azeotropically removed with isopropanol (2×500 mL). Tert-butyl methyl ether (300 mL) was added and the resulting slurry was stirred, filtered, washed with t-butyl methyl ether (3×100 mL) and dried to give 131.0 g (95.5%) of the title compound.

D. Preparation of α-Amino-pinacolone Hydrochloride

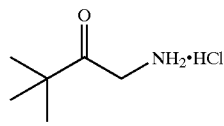

α-Hexamethylenetetramino-pinacolone bromide (400 g, 1.254 mol, 1 eq) was combined in 2 L of ethanol with 12 N aqueous HCl (439 mL, 5.26 mol, 4.2 eq). The reaction was stirred at 75° C. for 1 hour and then allowed to cool to room temperature, the resulting slurry filtered, the filtrate concentrated in vacuo and isopropyl alcohol was added. The solution was filtered again. Addition of 1.2 L of ether caused the desired material to precipitate from solution. The material was filtered, washed with ether (2×300 mL), and dried in vacuo at 50° C. overnight to provide 184.1 g (97%) of the title compound.

E. Preparation of α-N-(2-Chloroacetylamino)-pinacolone

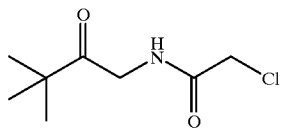

The title compound of part D (130.96 g, 0.8637 mol, 1 eq) was dissolved in 3.025 L of $CH_2Cl_2$ under $N_2$ at −5° C. Triethylamine (301 mL, 2.16 mol, 2.5 eq) was added, followed by chloroacetyl chloride (75.7 mL, 0.450 mol, 1.1 eq) in 175 mL of $CH_2Cl_2$. The resulting slurry was stirred at −5 to −10° C. for 2 hours. Water (1.575 L) was added, followed by 175 mL of concentrated HCl. The organic phase was washed a second time with 1.75 L of 10% aqueous HCl, and then with 500 mL of water. The organic phase was dried over $Na_2SO_4$ and concentrated in vacuo to provide 155.26 g (93.8%) of the title compound. HPLC R.T.=2.27 min (Phenomenex Inc., 5 μm C18 column 4.6×50 mm, 10–90% aqueous methanol over 4 minutes containing 0.2% phosphoric acid, 4 mL/min, monitoring at 220 nm).

F. Preparation of 5-(t-Butyl)-2-Oxazolylmethyl Chloride

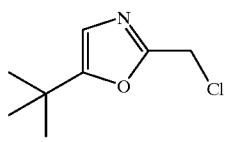

The title compound of part E (I180.13 g, 0.9398 mol, 1 eq) was combined with phosphorus oxychloride (262 mL, 2.8109 mol, 3 eq) under $N_2$. The reaction was heated at 105° C. for 1 hour, the mixture was cooled to room temperature, and quenched with 1.3 kg of ice. The aqueous phase was extracted with ethyl acetate (1 L, then 2×500 mL). The organic extracts were washed with saturated aqueous $NaHCO_3$ (4×1 L) which was back-extracted several times with ethyl acetate. The organic phases were combined, washed with saturated aqueous $NaHCO_3$ (500 mL) followed by saturated aqueous NaCl (300 mL), dried over $MgSO_4$, and concentrated in vacuo to give a brown oil. The crude material was distilled under high vacuum at 100° C. to provide 155.92 g (96%) of the title compound. HPLC R.T.=3.62 min (Phenomenex Inc., 5 μm C18 column 4.6×50 mm, 10–90% aqueous methanol over 4 minutes containing 0.2% phosphoric acid, 4 mL/min, monitoring at 220

Alternatively, the title compound of part E (10.0 g, 52.17 mmol, 1 eq.) in 50 mL of tetrahydrofuran (THF) was combined with (methoxycarbonylsulfamyl)-triethylammonium hydroxide (Burgess' reagent, 105.70 mmol, 2.03 eq., generated in situ from 9.2 mL of chlorosulfonyl isocyanate, 4.4 mL of methanol and 14.8 mL of triethylamine in 100 mL THF). The reaction was heated to 45° C. for 1.5 hours. After cooling to room temperature, the reaction was quenched with water (50 mL). The organic layer was separated and washed with saturated $NaHCO_3$ (2×50 mL) and water (50 mL), dried over $MgSO_4$ and passed through a small silica gel plug. The solvent was removed to give an oil which was taken up in a mixture of 15 mL heptane and 90 mL of t-butyl methyl ether, and then washed with 0.2 N HCl (2×25 mL), saturated brine (25 mL) and dried ($MgSO_4$). Filtration and removal of solvent gave 10.9 g of the title compound.

G. Preparation of 5-(t-Butyl)-2-oxazolylmethyl Thiouronium Hydrochloride

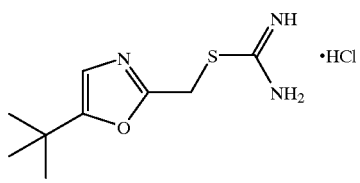

The title compound of part F (1.77 g, 10.2 mmol, 1.02 eq) was combined with thiourea (0.76 g, 9.98 mmol, 1 eq) under $N_2$ in 10 mL of absolute ethanol. The reaction was heated at reflux for 1.5 hours. The mixture was cooled to room temperature and concentrated in vacuo. Trituration of the resulting crude material with t-butyl methyl ether provided 2.32 g (93%) of the title compound. HPLC R.T.=2.05 min (Phenomenex Inc., 5 μm C18 column 4.6×50 mm, 10–90% aqueous methanol over 4 minutes containing 0.2% phosphoric acid, 4 mL/min, monitoring at 220 nm);

$^1$H NMR ($d_6$-DMSO): δ 9.48 (s, 3H), 6.85 (s, 1H), 4.73 (s, 2H), 1.24 (s, 9H).

H. Preparation of 5-[5-(t-Butyl)-2-oxazolylmethylthio]-2-aminothiazole

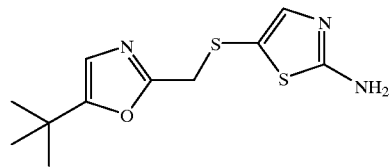

The title compound of part G (1.25 g, 5 mmol, 1 eq) was added to a mixture of NaOH (3.0 g, 75 mmol, 15 eq), water (10 mL), toluene (10 mL) and tetrabutylammonium sulfate (50 mg, 0.086 mmol, 0.017 eq). 5-Bromo-2-aminothiazole hydrobromide (1.70 g, 5 mmol, 1 eq) was added and the reaction was stirred at room temperature for 14.5 hours. The mixture was diluted with water and extracted twice with ethyl acetate, the organic extracts washed with water (4×10 mL), dried over $MgSO_4$ and concentrated in vacuo to provide 1.1 g (82%) of the title compound. HPLC 86.3% at 2.75 min (Phenomenex Inc., 5 μm C18 column 4.6×50 mm, 10–90% aqueous methanol over 4 minutes containing 0.2% phosphoric acid, 4 mL/min, monitoring at 220 nm);

$^1$H NMR (CDCl$_3$): δ 6.97 (s, 1H), 6.59 (s, 1H), 5.40 (br s, 2H), 3.89 (s, 2H), 1.27 (s, 9H).

I. Preparation of 5-[5-(t-Butyl)-2-oxazolylmethylthio]-2-[(N-t-butoxycarbonyl)-azacyloalkanoyl]aminothiazole

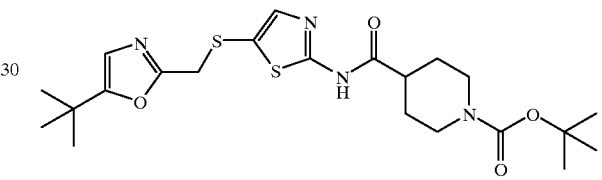

The title compound of part H (9.6 g, 35.6 mmol) was dissolved in N,N-dimethylformamide (36 mL) and CH$_2$Cl$_2$ (100 mL), to which was added 1-(3-dimethylaminopropyl)-3-ethylcarbodiimide hydrochloride (13.8 g, 72 mmol, 2 eq), N-t-butoxycarbonyl-azacycloalkanoic acid (12.6 g, 55 mmol, 1.5 eq), and 4-(dimethylamino)pyridine (2 g, 16 mmol, 0.45 eq). The clear reaction mixture became cloudy as it was stirred at room temperature for 3.5 hours. Water (300 mL) and ethyl acetate (200 mL) were added and the resulting precipitate was removed by filtration. The filtrate was extracted with ethyl acetate, the organic extracts dried over MgSO$_4$ and concentrated in vacuo to provide a yellow solid which was combined with the precipitate obtained by filtration. The solid was boiled in a mixture of ethanol, acetone and water for 20 minutes, filtered, washed with an ethanol/water mixture and dried to give 16.6 g (97%) of the title compound.

J. Preparation of 5-[5-(t-Butyl)-2-oxazolylmethylthio]-2-(azacycloalkanoyl)aminothiazole hydrochloride

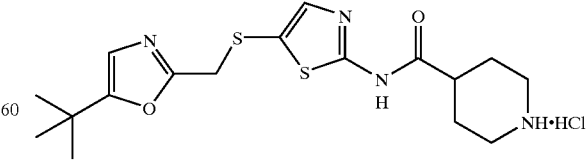

The title compound of part I (16.6 g) was dissolved in 150 mL of CH$_2$Cl$_2$, trifluoroacetic acid (30 mL) was added dropwise, and the mixture was stirred at room temperature for 2 hours. The reaction was concentrated in vacuo, diluted with water (300 mL), cooled in ice, made basic with sodium hydroxide, and the resulting solid filtered and recrystallized from ethanol, water and methanol to provide 11.2 g (83%) of the title compound as a yellow solid. The white solid hydrochloride could be obtained by addition of 18 mL of 1N aqueous HCl to 7 g of this material in methanol. MS: 381 [M+H]$^+$; HPLC: 100% at 3.12 min (YMC S5 ODS column 4.6×50 mm, 10–90% aqueous methanol over 4 minutes containing 0.2% phosphoric acid, 4 mL/min, monitoring at 220 nm).

EXAMPLE 2

Preparation of (±)-N-[5-[[[5-(1,1-Dimethylethyl)-2-oxazolyl]-methyl]thio]-2-thiazolyl]-3-piperidinecarboxamide

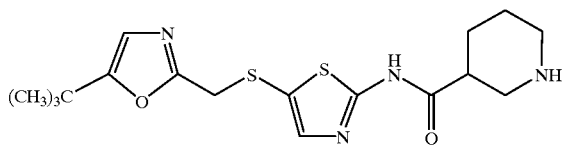

A. (±)-N-t-butoxycarbonyl-nipecotic acid

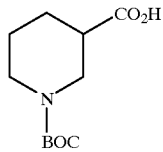

Nipecotic acid (1.3 g, 10 mmol, 1 eq) was combined with 10 mL of dioxane, 2 mL of acetonitrile, 10 mL of water, and 10 mL of 1N aqueous NaOH (1 eq). Di-t-butyl dicarbonate (3.3 g, 15 mmol, 1.5 eq) was added and the reaction mixture was stirred at rt overnight. The reaction mixture was concentrated in vacuo to remove organic solvent and 10% aqueous citric acid was added The mixture was extracted with ethyl acetate (3×100 mL). The organic extracts were dried over Na$_2$SO$_4$, filtered through silica gel, and concentrated in vacuo. The crude material was recrystallized from ethyl acetate and hexanes to provide 2.2 g (96%) of (±)-N-t-butoxycarbonyl-nipecotic acid as a white solid.

B. (±)-N-[5-[[[5-(1,1-Dimethylethyl)-2-oxazolyl]methyl]thio]-2-thiazolyl]-(N-t-butoxycarbonyl)-3-piperidinecarboxamide

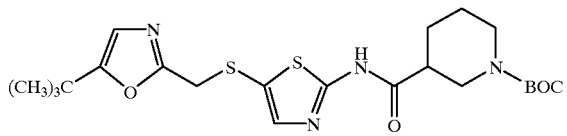

1-(3-Dimethylaminopropyl)-3-ethylcarbodiimide hydrochloride (383 mg, 2 mmol, 2 eq) was added to a mixture of 2-amino-5-[[[5-(1,1-dimethylethyl)-2-oxazolyl]methyl]thio]thiazole (270 mg, 1 mmol, 1 eq), N-t-butoxycarbonyl-nipecotic acid (344 mg, 1.5 mmol, 1.5 eq), 4-(dimethylamino)pyridine (61 mg, 0.5 mmol, 0.5 eq), N,N-dimethylformamide (1 mL) and CH$_2$Cl$_2$ (6 mL). The reaction mixture was stirred at rt for 1.3 h. Triethylamine (0.28 mL, 2 mmol, 2 eq) was added, and the reaction mixture was stirred for 1 h. Additional N-t-butoxycarbonyl-nipecotic acid (340 mg), triethylamine (0.28 mL) and 1-(3-dimethylaminopropyl)-3-ethylcarbodiimide hydrochloride (380 mg) were added. After 1 h, no further change was observed. Additional 4-(dimethylamino)pyridine, N,N-dimethylformamide, triethylamine and starting acid were added and the reaction was stirred overnight at rt. The resulting black solution was diluted with saturated aqueous NaHCO$_3$ and extracted with CH$_2$Cl$_2$. The organic extracts were dried, concentrated in vacuo, and purified by flash chromatography on silica gel eluting with a gradient of 50–100% ethyl acetate in hexanes to provide 397 mg (83%) of (±)-N-[5-[[[5-(1,1-dimethylethyl)-2-oxazolyl]methyl]thio]-2-thiazolyl]-(N-t-butoxycarbonyl)-3-piperidinecarboxamide as a yellow glassy solid.

C. (±)-N-[5-[[[5-(1,1-Dimethylethyl)-2-oxazolyl]methyl]thio]-2-thiazolyl]-3-piperidinecarboxamide

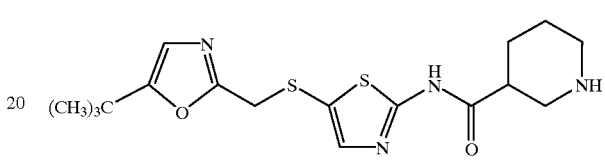

(±)-N-[5-[[[5-(1,1-Dimethylethyl)-2-oxazolyl]methyl]thio]-2-thiazolyl]-(N-t-butoxycarbonyl)-3-piperidinecarboxamide (355 mg, 0.74 mmol, 1 eq) was dissolved in 3 mL of CH$_2$Cl$_2$. Trifluoroacetic acid (3 mL) was added, and the mixture was stirred at rt for 20 min. The reaction mixture was concentrated in vacuo and neutralized with saturated aqueous NaHCO$_3$. The resulting mixture was extracted with ethyl acetate. The organic extracts were dried over Na$_2$SO$_4$, concentrated in vacuo, and recrystallized from ethyl acetate to provide 142 mg (50%) of (±)-N-[5-[[[5-(1,1-dimethylethyl)-2-oxazolyl]methyl]thio]-2-thiazolyl]-3-piperidinecarboxamide as a white solid. MS: 381 [M+H]$^+$; HPLC: 100% at 3.15 min (YMC S5 ODS column 4.6×50 mm, 10–90% aqueous methanol over 4 minutes containing 0.2% phosphoric acid, 4 mL/min, monitoring at 220 nm).

EXAMPLE 3

Preparation of (±)-1-(2,3-Dihydroxypropyl)-N-[5-[[[5-(1,1-dimethylethyl)-2-oxazolyl]methyl]thio]-2-thiazolyl]-4-piperidinecarboxamide

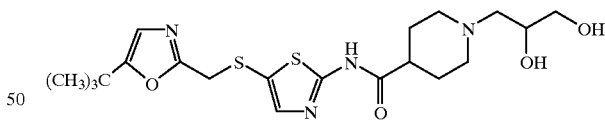

N-[5-[[[5-(1,1-Dimethylethyl)-2-oxazolyl]methyl]thio]-2-thiazolyl]-4-piperidinecarboxamide (66 mg, 0.17 mmol, 1 eq) was combined with glyceraldehyde (69 mg, 0.77 mmol, 4.5 eq), sodium triacetoxyborohydride (163 mg, 0.77 mmol, 4.5 eq) and 1,2-dichloroethane (4 mL). The resulting suspension was stirred at rt for 4 h. Methanol (1 mL) was added and the reaction mixture was stirred at rt overnight, concentrated in vacuo and purified by preparative HPLC to provide 69 mg (59%) of(±)-1-(2,3-dihydroxypropyl)-N-[5-[[[5-(1,1-dimethylethyl)-2-oxazolyl]methyl]thio]-2-thiazolyl]-4-piperidinecarboxamide as a white solid. MS: 455 [M+H]$^+$; HPLC: 100% at 3.06 min (YMC S5 ODS column 4.6×50 mm, 10–90% aqueous methanol over 4 minutes containing 0.2% phosphoric acid, 4 mL/min, monitoring at 220 nm).

EXAMPLE 4

Preparation of N-[5-[[[5-(1,1-Dimethylethyl)-2-oxazolyl]methyl]thio]-2-thiazolyl]-1-(1-methylethyl)-4-piperidinecarboxamide

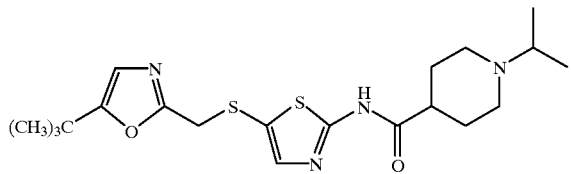

A. Ethyl-1-(1-methylethyl)-4-piperidine carboxylate

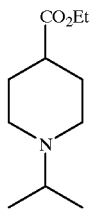

Ethyl isonipecotate (3.2 g, 20 mmol, 1 eq) was combined with acetone (5.8 g, 100 mmol, 5 eq), sodium triacetoxyborohydride (10.5 g, 50 mmol, 2.5 eq) and 1,2-dichloroethane (200 mL). The reaction mixture was stirred at rt for 72 h. Saturated aqueous NaHCO$_3$ was added, and the mixture was extracted with CH$_2$Cl$_2$. The organic extracts were dried, filtered through a silica gel pad, and concentrated in vacuo to provide 3.72 g (93%) of ethyl 1-(1-methylethyl)-4-piperidine carboxylate as a colorless liquid.

B. 1-(1-Methylethyl)-4-piperidine carboxylic acid

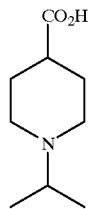

Ethyl 1-(1-methylethyl)-4-piperidine carboxylate (3.6 g, 18 mmol, 1 eq) was combined with barium hydroxide octahydrate (10.4 g, 33 mmol, 1.8 eq) in a mixture of 70 mL of water with 44 mL of ethanol. The mixture was heated at 60° C. for 1.3 h. The reaction mixture was concentrated in vacuo and diluted with 70 mL of water. Ammonium carbonate (6.9 g, 87 mmol, 4.8 eq) was added portionwise and the reaction mixture was stirred at rt overnight. The mixture was filtered through diatomaceous earth, concentrated, and lyophilized to provide 3.1 g (100%) of 1-(1-methylethyl)-4-piperidine carboxylic acid as a white solid.

C. N-[5-[[[5-(1,1-Dimethylethyl)-2-oxazolyl]methyl]thio]-2-thiazolyl]-1-(1-methylethyl)-4-piperidinecarboxamide

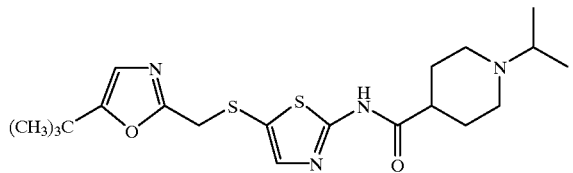

1-(3-Dimethylaminopropyl)-3-ethylcarbodiimide hydrochloride (1.0 g, 5.2 mmol, 2 eq) was added to a mixture of 2-amino-5-[[[5-(1,1-dimethylethyl)-2-oxazolyl]methyl]thio]thiazole (0.7 g, 2.6 mmol, 1 eq), 1-(1-methylethyl)-4-piperidine carboxylic acid (0.78 g, 3.9 mmol, 1.5 eq), 4-(dimethylamino)pyridine (0.16 g, 1.3 mmol, 0.5 eq), N,N-dimethylformamide (2.6 mL) and CH$_2$Cl$_2$ (7.8 mL). The reaction mixture was stirred at rt for 1 h, diluted with 30 mL of water and extracted with ethyl acetate (2×70 mL). The organic extracts were dried over Na$_2$SO$_4$, concentrated in vacuo, and purified by flash chromatography on silica gel eluting with a gradient of 5–10% triethylamine in ethyl acetate. The material was recrystallized from ethanol and water to provide 0.93 g (85%) of N-[5-[[[5-(1,1-dimethylethyl)-2-oxazolyl]methyl]thio]-2-thiazolyl]- 1-(1-methylethyl)-4-piperidinecarboxamide as a yellowish solid. MS: 423 [M+H]$^+$; HPLC: 100% at 3.15 min (YMC S5 ODS column 4.6×50 mm, 10–90% aqueous methanol over 4 minutes containing 0.2% phosphoric acid, 4 mL/min, monitoring at 220 nm).

EXAMPLE 5

Preparation of 1-Cyclopropyl-N-[5-[[[5-(1,1-dimethylethyl)-2-oxazolyl]methyl]thiol]-2-thiazolyl]-4-piperidinecarboxamide

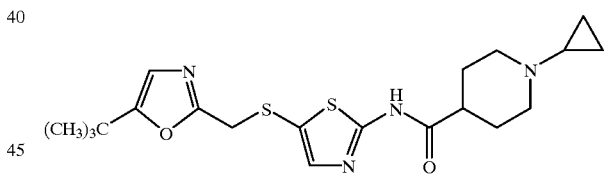

A. 1-Cyclopropyl-4-piperidine carboxylic acid

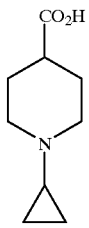

Ethyl isonipecotate (1.57 g, 10 mmol, 1 eq) was combined with ((1-ethoxycyclopropyl)oxy)trimethyl silane (8.7 g, 50 mmol, 5 eq) in 100 mL of methanol. Acetic acid (5.7 mL, 100 mmol, 10 eq) and molecular sieves were added. After 30 min at rt, sodium triacetoxyborohydride (2.5 g, 40 mmol, 4 eq) was added and the reaction mixture was heated at 65° C.

overnight. The reaction mixture was cooled and Na₂CO₃ (20 g) was added. The mixture was stirred at rt for 2 h and filtered through diatomaceous earth. The diatomaceous earth was washed with methanol. The filtrates were combined, concentrated in vacuo, diluted with water, and extracted with ethyl acetate. The organic extracts were dried, filtered through a silica gel pad, and concentrated in vacuo to provide 2.4 g of colorless liquid. This material was combined with barium hydroxide octahydrate (5.7 g, 18 mmol, 1.8 eq) in a mixture of 38 mL of water with 24 mL of ethanol. The mixture was heated at 60° C. for 1 h. The reaction mixture was concentrated in vacuo and diluted with 38 mL of water. Ammonium carbonate (3.8 g) was added portionwise and the reaction was stirred at rt for 2 h. The mixture was filtered through diatomaceous earth, washing with water. The filtrate was washed with ethyl acetate. Concentration of the aqueous phase provided 1.56 g (92%) of 1-cyclopropyl-4-piperidine carboxylic acid as a hygroscopic white solid.

B. 1-Cyclopropyl-N-[5-[[[5-(1,1-dimethylethyl)-2-oxazolyl]-methyl]thio]-2-thiazolyl]-4-piperidinecarboxamide

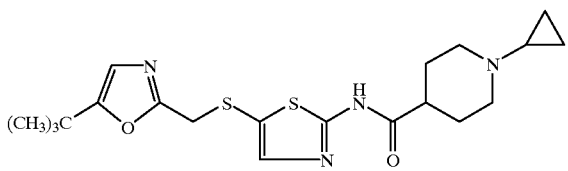

1-(3-Dimethylaminopropyl)-3-ethylcarbodiimide hydrochloride (1.0 g, 5.2 mmol, 2 eq) was added to a mixture of 2-amino-5-[[[5-(1,1-dimethylethyl)-2-oxazolyl]methyl]thio]thiazole (0.7 g, 2.6 mmol, 1 eq), 1-cyclopropyl-4-piperidine carboxylic acid (0.77 g, 3.9 mmol, 1.5 eq), 4-(dimethylamino)pyridine (0.16 g, 1.3 mmol, 0.5 eq), N,N-dimethylformamide (2.6 mL) and CH₂Cl₂ (7.8 mL). The reaction mixture was stirred at rt for 1 h, diluted with water (30 mL), and extracted with ethyl acetate (2×70 mL). The combined organic extracts were dried over anhydrous sodium sulfate, concentrated in vacuo, and purified by flash chromatography on silica gel eluting with a gradient of 0–10% triethylamine in ethyl acetate. The material was crystallized from ethyl acetate and hexanes to provide 0.7 g (65%) of 1-cyclopropyl-N-[5-[[[5-(1,1-dimethylethyl)-2-oxazolyl]methyl]thio]-2-thiazolyl]-4-piperidinecarboxamide as white crystals. MS: 421 [M+H]⁺; HPLC: 100% at 3.13 min (YMC S5 ODS column 4.6×50 mm, 10–90% aqueous methanol over 4 minutes containing 0.2% phosphoric acid, 4 mL/min, monitoring at 220 nm).

EXAMPLE 6

Preparation of N-[5-[[[5-(1,1-Dimethylethyl)-2-oxazolyl] methyl]thio]-2-thiazolyl]-1-(2-hydroxyethyl)-4-piperidinecarboxamide

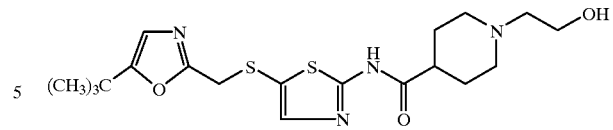

A. N-[5-[[[5-(1,1-Dimethylethyl)-2-oxazolyl]methyl]thio]-2-thiazolyl]-1-(2-dimethyl-t-butylsilyloxyethyl)-4-piperidinecarboxamide

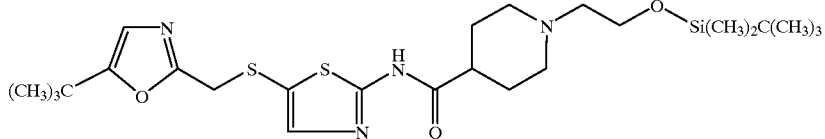

N-[5-[[[5-(1,1-dimethylethyl)-2-oxazolyl]methyl]thio]-2-thiazolyl]-4-piperidinecarboxamide (1.4 g, 3.68 mmol, 1 eq) was dissolved in 30 mL of N,N-dimethylformamide and 100 mL of tetrahydrofuran. 2-(Bromoethoxy)-t-butyldimethylsilane (0.79 mL, 3.68 mmol, 1 eq), and NaHCO₃ were added and the reaction mixture was stirred at 50° C. for 23 h. Additional 2-(bromoethoxy)-t-butyldimethylsilane (0.9 mL) was added, and the reaction mixture was stirred at 50° C. for 22 h, cooled, concentrated in vacuo and diluted with water (25 mL). The resultant aqueous mixture was extracted with ethyl acetate (50 mL). The organic extract was dried over Na₂SO₄, concentrated in vacuo, and purified by flash chromatography on silica gel eluting with a gradient of 0–5% triethylamine in ethyl acetate to provide 1.7 g (84%) of N-[5-[[[5-(1,1-dimethylethyl)-2-oxazolyl]methyl]thio]-2-thiazolyl]-1-(2-dimethyl-t-butylsilyloxyethyl)-4-piperidinecarboxamide as a yellow solid. MS: 539 [M+H]⁺; HPLC: 98% at 4.01 min (YMC S5 ODS column 4.6×50 mm, 10–90% aqueous methanol over 4 minutes containing 0.2% phosphoric acid, 4 mL/min, monitoring at 220 nm).

B. N-[5-[[[5-(1,1-Dimethylethyl)-2-oxazolyl]methyl]thio]-2-thiazolyl]-1-(2-hydroxyethyl)-4-piperidinecarboxamide

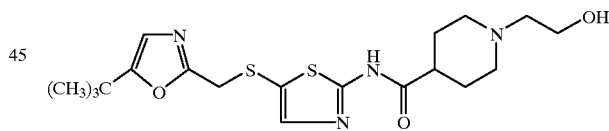

N-[5-[[[5-(1,1-Dimethylethyl)-2-oxazolyl]methyl]thio]-2-thiazolyl]-1-(2-dimethyl-t-butylsilyloxyethyl)-4-piperidinecarboxamide (1.45 g, 2.7 mmol, 1 eq) was dissolved in 100 mL of acetonitrile and combined with aqueous HF (48% aqueous, 2.5 mL). The reaction mixture was stirred for 4 h at rt. An additional 2.5 mL of aqueous HF was added, and the reaction mixture was stirred overnight. Ethyl acetate (100 mL) and saturated aqueous NaHCO₃ (50 mL) were added. Additional solid NaHCO₃ was added to make the mixture basic. The mixture was extracted with ethyl acetate (2×50 mL). The organic extracts were dried over Na₂SO₄, filtered through a pad of silica gel, and concentrated in vacuo. The resulting white solid was crystallized from ethanol and water to provide 1.6 g (59%) of N-[5-[[[5-(1,1-dimethylethyl)-2-oxazolyl]methyl]thio]-2-thiazolyl]-1-(2-hydroxyethyl)-4-piperidinecarboxamide as a white solid. MS: 425 [M+H]⁺; HPLC: 100% at 3.05 min (YMC S5 ODS column 4.6×50 mm, 10–90% aqueous methanol over 4

EXAMPLE 7
Preparation of (R)-N-[5-[[[5-(1,1-Dimethylethyl)-2-oxazolyl]methyl]thio]-2-thiazolyl]-3-piperidinecarboxamide hydrochloride

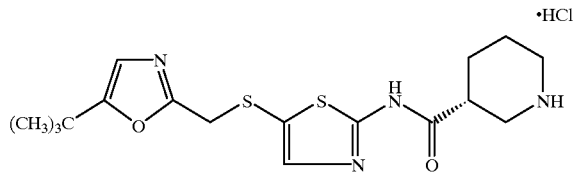

A. (R)- and (S)-N-[5-[[[5-(1,1-Dimethylethyl)-2-oxazolyl]methyl]thio]-2-thiazolyl-(N-t-butoxycarbonyl)-3-piperidinecarboxamide (R)
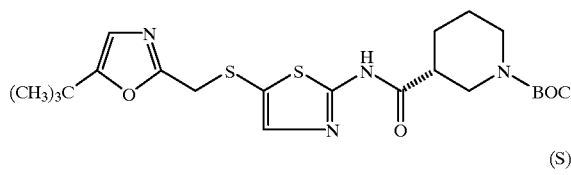

(S)
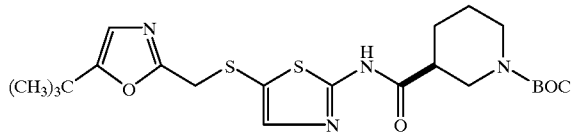

1-(3-Dimethylaminopropyl)-3-ethylcarbodiimide hydrochloride (3.8 g, 20 mmol, 2 eq) was added to a mixture of 2-amino-5-[[[5-(1,1-dimethylethyl)-2-oxazolyl]methyl]thio]thiazole (2.7 g, 10 mmol, 1 eq), N-t-butoxycarbonyl-nipecotic acid (3.4 g, 1.5 mmol, 1.5 eq), N,N-dimethylformamide (10 mL) and $CH_2Cl_2$ (30 mL). The reaction mixture was stirred at rt for 4 h. The resulting black solution was concentrated in vacuo, diluted with water (90 mL) and extracted with ethyl acetate (100 mL, then 2×75 mL). The organic extracts were dried over $Na_2CO_3$, concentrated in vacuo, and purified by flash chromatography on silica gel eluting with a gradient of 50–100% ethyl acetate in hexanes to provide 3.8 g (79%) of a yellow solid. The enantiomers were separated by chiral HPLC (Chiral Pak AD 5×50 cm 20 μ: eluent 10% (0.1% triethylamine in isopropanol) in hexanes; 45 mL/min, detection at 254 nm, loading 300 mg in 5 mL of isopropanol) to give each of the two optically pure isomers: 1.65 g of the R isomer and 1.65 g of the S isomer.

B. (R)-N-[5-[[[5-(1,1-Dimethylethyl)-2-oxazolyl]methyl]thio]-2-thiazolyl]-3-piperidinecarboxamide hydrochloride

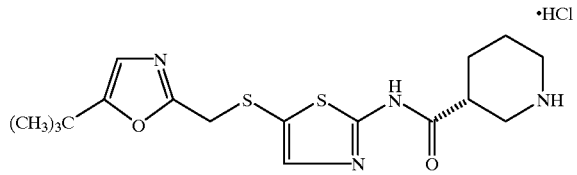

The (R) isomer of Part A (1.65 g, 3.43 mmol, 1 eq) was dissolved in 10 mL of $CH_2Cl_2$. Trifluoroacetic acid (6 mL) was added, and the mixture was stirred at rt for several hours. The reaction mixture was concentrated in vacuo and neutralized with saturated aqueous $NaHCO_3$. The resulting mixture was stirred with ethyl acetate for 1 h. The organic extracts were dried over $Na_2SO_4$ and concentrated in vacuo to provide a yellowish solid. The solid was dissolved in methanol and 1 eq of 1N aqueous HCl was added. The resulting solution was lyophilized to provide 1 g (77%) of (R)-N-[5-[[[5-(1,1-dimethylethyl)-2-oxazolyl]methyl]thio]-2-thiazolyl]-3-piperidinecarboxamide hydrochloride as a yellow solid. MS: 381 $[M+H]^+$; HPLC: 100% at 3.14 min (YMC S5 ODS column 4.6×50 mm, 10–90% aqueous methanol over 4 minutes containing 0.2% phosphoric acid, 4 mL/min, monitoring at 220 nm).

EXAMPLE 8
Preparation of (S)-N-[5-[[[5-(1,1-Dimethylethyl)-2-oxazolyl]-methyl]thio]-2-thiazolyl]-3-piperidine carboxamide hydrochloride

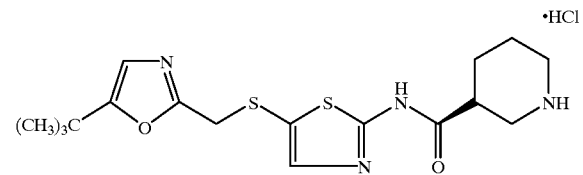

The (S) isomer of Example 7, Part A (1.65 g, 3.43 mmol, 1 eq) was dissolved in 10 mL of $CH_2Cl_2$. Trifluoroacetic acid (6 mL) was added, and the mixture was stirred at rt for several hours. The reaction was concentrated in vacuo and neutralized with saturated aqueous $NaHCO_3$. The resulting mixture was stirred with ethyl acetate for 1 h. The organic extracts were dried over $Na_2SO_4$ and concentrated in vacuo to provide a yellowish solid. The solid was dissolved in methanol and 1 eq of 1N aqueous HCl was added. The resulting solution was lyophilized to provide 0.918 g (70%) of (S)-N-[5-[[[5-(1,1-dimethylethyl)-2-oxazolyl]methyl]thio]-2-thiazolyl]-3-piperidinecarboxamide hydrochloride as a yellow solid. MS: 381 $[M+H]^+$; HPLC: 100% at 3.15 min (YMC S5 ODS column 4.6×50 mm, 10–90% aqueous methanol over 4 minutes containing 0.2% phosphoric acid, 4 mL/min, monitoring at 220 nm).

EXAMPLE 9
Preparation of cis-4-Amino-N-[5-[[[5-(1,1-dimethylethyl)-2-oxazolyl]-methyl]thio]-2-thiazolyl]cyclohexylcarboxamide hydrochloride and trans-4-Amino-N-[5-[[[5-(1,1-dimethylethyl)-2-oxazolyl]methyl]thio]-2-thiazolyl]-cyclohexylcarboxamide hydrochloride

A. 4-(t-Butoxycarbonylamino)cyclohexane carboxylic acid

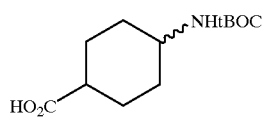

To a solution of 2.86 g (20 mmol) of 4-aminocyclohexane carboxylic acid in 40 mL of 0.5M aqueous NaOH solution, 20 mL of dioxane and 4 mL of acetonitrile was added a total of 6.5 g (30 mmol) of tBoc anhydride at room temperature. After 20 h, 100 mL of ethyl acetate and 100 mL of 10% aqueous citric acid solution were introduced. The aqueous layer which formed was separated and extracted with three-50 mL portions of ethyl acetate. The organic phases were combined, dried (sodium sulfate) and concentrated in vacuo to give 6.0 g (125%) of crude 4-(t-butoxycarbonylamino) cyclohexane carboxylic acid as a colorless oil which solidified upon standing.

B. 4-(t-Butoxycarbonylamino)-N-[5-[[[5-(1,1-dimethylethyl)-2-oxazolyl]-methyl]thio]-2-thiazolyl] cyclohexylcarboxamide

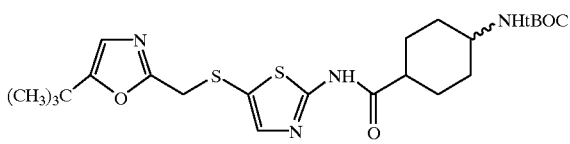

To a solution of 5 g of crude 4-(t-butoxycarbonylamino) cyclohexane carboxylic acid and 3.50 g (13 mmol) of 2-amino-5-[[[5-(1,1-dimethylethyl)-2-oxazolyl]methyl] thio]thiazole in 13 mL of N,N-dimethylformamide and 36 mL of methylene chloride was added 5.0 g (26 mmol) of 1-(3-dimethylaminopropyl)-3-ethylcarbodiimide hydrochloride at room temperature. The reaction mixture was stirred overnight and diluted with 100 mL of water. The aqueous layer was separated and extracted with two-150 mL portions of ethyl acetate. The combined organic phases were dried (sodium sulfate) then filtered through a pad of silica gel. The filtrate was concentrated in vacuo to afford an orange solid. The crude material was recrystallized (95% ethanol) to give 4-(t-butoxycarbonylamino)-N-[5-[[[5-(1,1-dimethylethyl)-2-oxazolyl]methyl]thio]-2-thiazolyl] cyclohexylcarboxamide as a yellow solid. The mother liquors were also concentrated in vacuo to give additional 4-(t-butoxycarbonylamino)-N-[5-[[[5-(1,1-dimethylethyl)-2-oxazolyl]methyl]thio]-2-thiazolyl] cyclohexylcarboxamide as a brown solid.

C. cis-4-Amino-N-[5-[[[5-(1,1-dimethylethyl)-2-oxazolyl] methyl]thio]-2-thiazolyl]cyclohexylcarboxamide hydrochloride and trans-4-Amino-N-[5-[[[5-(1,1-dimethylethyl)-2-oxazolyl]methyl]thio]-2-thiazolyl]-cyclohexylcarboxamide hydrochloride

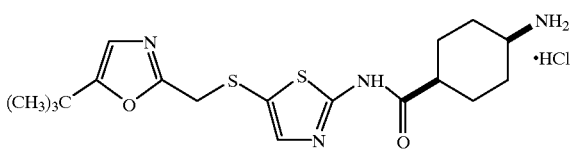

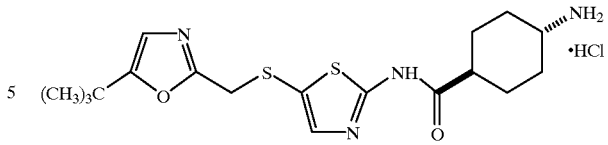

To a suspension of 4-(t-butoxycarbonylamino)-N-[5-[[[5-(1,1-dimethylethyl)-2-oxazolyl]methyl]thio]-2-thiazolyl] cyclohexylcarboxamide (from Part B mother liquors) suspended in 15 mL of methylene chloride was added 5 mL of trifluoroacetic acid at room temperature. The reaction mixture was stirred for 2 h then concentrated in vacuo to remove volatiles. The residue was diluted with water, basified with aqueous NaOH solution then the resulting aqueous solution was extracted with ethyl acetate. The combined organic extracts were dried (sodium sulfate) to give a crude cis/trans product. The crude material was purified by flash chromatography (Merck silica, 25×3 cm, 1:9 isopropylamine/ethyl acetate then 1:2:7 methanol/isopropylamine/ethyl acetate) to afford 0.74 g of the cis isomer as a yellow solid and 0.50 g of the trans isomer as a brown solid. The cis isomer was dissolved in methanol then 0.34 mL of 5N aqueous HCl was added. The solution was concentrated in vacuo, washed with ether, diluted with water and lyophilized to afford 0.80 g of cis-4-amino-N-[5-[[[5-(1,1-dimethylethyl)-2-oxazolyl] methyl]thio]-2-thiazolyl]cyclohexylcarboxamide hydrochloride as a yellow solid. MS: 395 [M+H]$^+$; HPLC-HI 98% at 3.17 min (YMC S5 ODS column 4.6×50 mm, 10–90% aqueous methanol over 4 minutes containing 0.2% phosphoric acid, 4 mL/min, monitoring at 220 nm). The trans isomer was dissolved in methanol then 0.24 mL of 5N aqueous HCl was added. The solution was concentrated in vacuo, washed with ether, diluted with water and lyophilized to afford 0.54 g of trans-4-amino-N-[5-[[[5-(1,1-dimethylethyl)-2-oxazolyl]methyl]thio]-2-thiazolyl] cyclohexylcarboxamide hydrochloride as an orange solid. MS: 395 [M+H]$^+$; HPLC-HI 96% at 3.22 min (YMC S5 ODS column 4.6×50 mm, 10–90% aqueous methanol over 4 minutes containing 0.2% phosphoric acid, 4 mL/min, monitoring at 220 nm).

EXAMPLE 10
N-[5-[[[5-(1,1-Dimethylethyl)-2-oxazolyl]methyl]thio]-2-thiazolyl]-4-piperidinecarboxamide, monohydrochloride

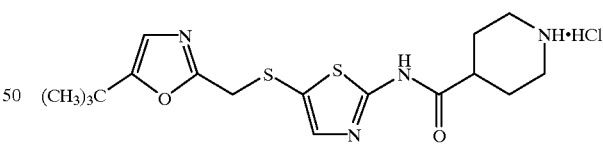

To a solution of 40 mL of absolute EtOH cooled in an ice-bath was added acetyl chloride (0.28 mL, 3.9 mmol) dropwise. The reaction mixture was allowed to warm to room temperature over 30 min then N-[5-[[[5-(1,1-dimethylethyl)-2-oxazolyl]methyl]-thio]-2-thiazolyl]-4-piperidinecarboxamide (1.50 g, 3.94 mmol, 1 eq) was introduced in one portion with stirring to give a thick slurry. Water (~4 mL) was added until homogeneous then concentrated in vacuo to give a crude pale yellow solid. The crude material was recrystallized (aq EtOH) to afford the title compound (70%) as a white solid, mp 256–258°.

Analysis calc'd for $C_{17}H_{24}N_4O_2S_2 \cdot HCl$: C, 48.96; H, 6.04; N, 13.43; S, 15.38; Cl, 8.50. Found: C, 48.69; H, 5.99; N, 13.24; S, 15.27; Cl, 8.31.

EXAMPLE 11
N-[5-[[[5-(1,1-Dimethylethyl)-2-oxazolyl]methyl]thio]-2-thiazolyl]-4-piperidinecarboxamide, monohydrobromide

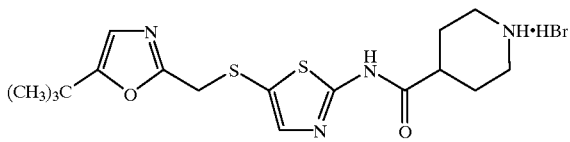

To a solution of 1M HBr in EtOH (0.5 mL) was added N-[5-[[[5-(1,1-dimethylethyl)-2-oxazolyl]methyl]thio]-2-thiazolyl]-4-piperidinecarboxamide (190 mg, 0.5 mmol, 1 eq) then cooled to −40° C. overnight. The solid precipitate that formed was collected on a Buchner funnel, washed with absolute EtOH then dried under vacuum at 100° C. to afford the title compound (72%) as a fine white powder, mp 235–237° C.

Analysis calc'd for C17H24N4O2S2·HBr: C, 44.24; H, 5.46; N, 12.14; S, 13.89; Br, 17.31. Found: C, 44.16; H, 5.40; N, 12.12; S, 13.91; Br, 17.70.

EXAMPLE 12
N-[5-[[[5-(1,1-Dimethylethyl)-2-oxazolyl]methyl]thio]-2-thiazolyl]-4-piperidinecarboxamide, 0.5-L-tartaric acid salt

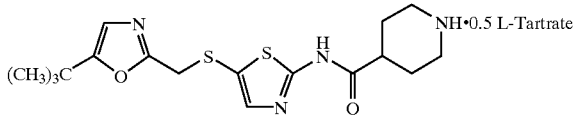

To a warm solution of N-[5-[[[5-(1,1-dimethylethyl)-2-oxazolyl]methyl]thio]-2-thiazolyl]-4-piperidinecarboxamide (1.75 g, 4.6 mmol) in absolute EtOH (70 mL) was added a solution of L-tartaric acid (345 mg, 2.3 mmol, 0.5 eq) in absolute EtOH (5 mL). A precipitate started to form after several minutes. The mixture was allowed to stand for 4 hr at room temperature then the solid precipitate was collected on a Buchner funnel, washed with absolute EtOH and dried under vacuum at 85° C. for 24 hr to afford the title compound (94%) as pale yellow crystals, mp 234–236° C.

Analysis calc'd for C17H24N4O2S2·0.5-L-Tartaric acid: C, 50.09; H, 5.97; N, 12.29; S, 14.07. Found: C, 49.85; H, 5.90; N, 12.12; S, 13.75.

EXAMPLE 13
N-[5-[[[5-(1,1-Dimethylethyl)-2-oxazolyl]methyl]thio]-2-thiazolyl]-4-piperidinecarboxamide, 0.5-D-tartaric acid salt

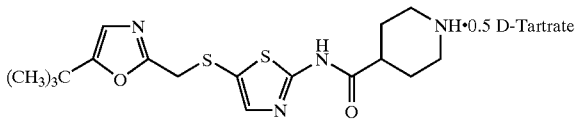

To a warm solution of N-[5-[[[5-(1,1-dimethylethyl)-2-oxazolyl]methyl]thio]-2-thiazolyl]-4-piperidinecarboxamide (1.00 g, 2.63 mmol) in absolute EtOH (40 mL) was added a solution of D-tartaric acid (198 mg, 1.32 mmol, 0.5 eq) in absolute EtOH (4 mL). A precipitate started to form after several minutes. The mixture was allowed to stand for 18 hr at room temperature then the solid precipitate was collected on a Buchner funnel, washed with absolute EtOH and dried under vacuum at 65° C. for 6 hr to afford the title compound (73%) as a white solid, mp 232–233° C.

Analysis calc'd for C17H24N4O2S2·0.5-D-Tartaric acid: C, 50.09; H, 5.97; N, 12.29; S, 14.07. Found: C, 49.75; H, 5.81; N, 12.04; S, 13.37.

EXAMPLE 14
N-[5-[[[5-(1,1-Dimethylethyl)-2-oxazolyl]methyl]thio]-2-thiazolyl]-4-piperidinecarboxamide, 0.5-fumaric acid salt

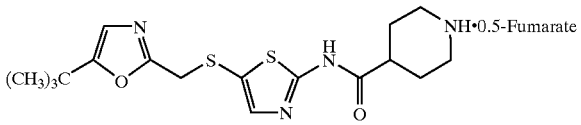

To a warm solution of N-[5-[[[5-(1,1-dimethylethyl)-2-oxazolyl]methyl]thio]-2-thiazolyl]-4-piperidinecarboxamide (1.75 g, 4.6 mmol) in absolute EtOH (100 mL) was added a solution of fumaric acid (276 mg, 2.3 mmol, 0.5 eq) in absolute EtOH (5 mL). A precipitate started to form after 10 minutes. The mixture was allowed to stand for 2 hr at room temperature then at 5° C. for 16 hr. The solid precipitate which formed was collected on a Buchner funnel, washed with absolute EtOH and dried under vacuum at 65° C. for 24 hr to afford the title compound (84%) as a white solid, mp 206–207° C.

Analysis calc'd for C17H24N4O2S2·0.5-Fumaric acid: C, 52.04; H, 5.98; N, 12.77; S, 14.62. Found: C, 51.74; H, 5.76; N, 12.57; S, 14.19. Recrystallization (95% aq EtOH) afforded the title compound containing 1 mol EtOH (83%) as large colorless crystals, mp 212–214° C.

Analysis calc'd for C17H24N4O2S2·0.5-Fumaric acid·EtOH: C, 52.05; H, 6.66; N, 11.56; S, 13.23. Found: C, 52.03; H, 6.06; N, 11.50; S, 12.99.

EXAMPLE 15
N-[5-[[[5-(1,1-Dimethylethyl)-2-oxazolyl]methyl]thio]-2-thiazolyl]-4-piperidinecarboxamide, 0.5-succinic acid salt

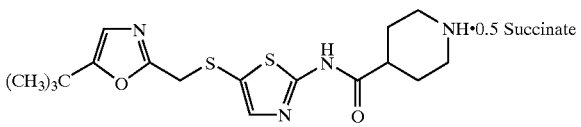

To a warm solution of N-[5-[[[5-(1,1-dimethylethyl)-2-oxazolyl]methyl]thio]-2-thiazolyl]-4-piperidinecarboxamide (50 mg, 0.13 mmol) in absolute EtOH (2 mL) was added a solution of succinic acid (7.7 mg, 0.065 mmol, 0.5 eq) in absolute EtOH (0.25 mL). A precipitate started to form after 10 minutes. The mixture was allowed to stand for 1 hr at room temperature then the precipitate was collected on a Buchner funnel, washed with absolute EtOH and dried under vacuum at 100° C. for 24 hr to afford the title compound (70%) as a white solid, mp 190–192° C.

Analysis calc'd for C17H24N4O2S2·0.5-Succinic acid·0.46H2O: C, 50.96; H, 6.28; N, 12.51; S, 14.32. Found: C, 50.96; H, 6.20; N, 12.49; S, 14.23.

EXAMPLE 16
N-[5-[[[5-(1,1-Dimethylethyl)-2-oxazolyl]methyl]thio]-2-thiazolyl]-4-piperidinecarboxamide, 0.5-sulfuric acid salt

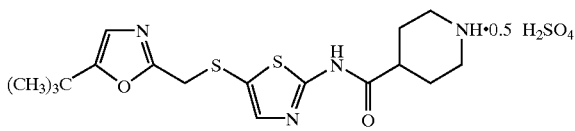

To a warm solution of N-[5-[[[5-(1,1-dimethylethyl)-2-oxazolyl]methyl]thio]-2-thiazolyl]-4-piperidinecarboxamide (50 mg, 0.13 mmol) in absolute EtOH (2 mL) was added a 1M aq solution of sulfuric acid (0.065 mL, 0.065 mmol, 0.5 eq ). A precipitate formed almost immediately. The mixture was cooled to 5° C. for 2 hr then the precipitate was collected on a Buchner funnel, washed with absolute EtOH and dried under vacuum at 100° C. for 24 hr to afford the title compound (79%) as a white solid, mp 256–258° C.

Analysis calc'd for C17H24N4O2S2·0.5H2SO4·0.68H2O: C, 46.22; H. 6.01; N, 12.68; S, 18.14. Found: C, 46.21; H, 5.95; N, 12.71; S, 18.23.

EXAMPLE 17
N-[5-[[[5-(1,1-Dimethylethyl)-2-oxazolyl]methyl]thio]-2-thiazolyl]-4-piperidinecarboxamide, 0.5-citric acid salt

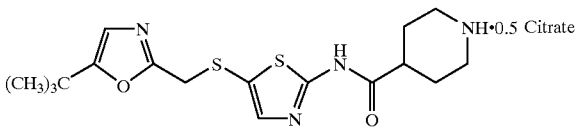

To a warm solution of N-[5-[[[5-(1,1-dimethylethyl)-2-oxazolyl]methyl]thio]-2-thiazolyl]-4-piperidinecarboxamide (50 mg, 0.13 mmol) in absolute EtOH (2 mL) was added a solution of citric acid (8.3 mg, 0.043 mmol, 0.33 eq ). The solution was cooled to 5° C. for 18 hr then the precipitate which formed was collected on a Buchner funnel, washed with absolute EtOH and dried under vacuum at 100° C. for 24 hr to afford the title compound (68%) as a white solid, mp 214–216° C.

Analysis calc'd for C17H24N4O2S2·0.5-Citric acid·0.10H2O: C, 50.21; H, 5.94; N, 11.71; S, 13.40. Found: C, 50.21; H, 6.01; N, 11.83; S, 13.44.

EXAMPLE 18
N-[5-[[[5-(1,1-Dimethylethyl)-2-oxazolyl]methyl]thio]-2-thiazolyl]-4-piperidinecarboxamide, methanesulfonic acid salt

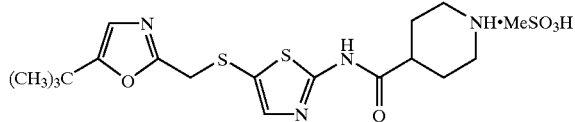

To a slurry of N-[5-[[[5-(1,1-dimethylethyl)-2-oxazolyl]methyl]thio]-2-thiazolyl]-4-piperidinecarboxamide (100 mg, 0.26 mmol) in isopropyl alcohol (0.75 mL) was added methanesulfonic acid (0.017 mL, 0.26 mmol, 1 eq). The slurry was heated to 70° C. to give a clear solution then methyl t-butyl ether (1.5 mL) was added. Within 15 minutes a precipitate formed. The resulting mixture was stirred at 55° C. for 2 hr then at room temperature for 14 hr. The precipitate which formed was collected by filtration then dried under vacuum at 50° C. for 14 hr to afford the title compound (85%) as a colorless powder, mp 105° C.

Analysis calc'd for C17H24N4O2S2·MSA·H2O: C, 43.70; H, 6.11; N, 11.32; S, 19.44. Found: C, 43.53; H, 6.14; N, 11.15; S, 19.15.

EXAMPLE 19
N-[5-[[[5-(1,1-Dimethylethyl)-2-oxazolyl]methyl]thio]-2-thiazolyl]-4-piperidinecarboxamide, 0.5-D,L-malic acid salt

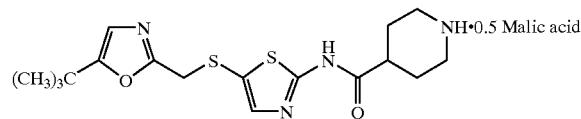

To a solution of N-[5-[[[5-(1,1-dimethylethyl)-2-oxazolyl]methyl]thio]-2-thiazolyl]-4-piperidinecarboxamide (100 mg, 0.26 mmol) in isopropyl alcohol (0.80 mL) was added slowly at 70° C. a solution of D,L-malic acid (35 mg, 0.13 mmol, 0.5 eq ) in isopropyl alcohol (0.3 mL). A precipitate formed immediately. The resulting mixture was stirred at 55° C. for 2 hr then at room temperature for 14 hr. The precipitate was collected by filtration then dried under vacuum at 50° C. for 14 hr to afford the title compound (75%) as a colorless powder, mp 216° C.

Analysis calc'd for C17H24N4O2S2·0.5-C4H6O5·H2O: C, 50.98; H, 6.08; N, 12.51; S, 14.32. Found: C, 50.55; H, 6.17; N, 12.29; S, 14.05.

We claim:
1. A method for preventing or treating alopecia induced by chemotherapy or radiotherapy which comprises administering to a mammalian specie in need thereof a therapeutically effective amount of a compound of formula I or II

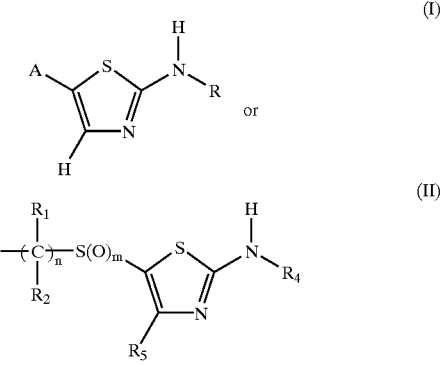

or a pharmaceutically acceptable salt thereof wherein

R is $R_6$, $COR_7$, $CONH_2$, $CONR_6R_7$, $COOR_6$ or $SO_2R_6$;

$R_6$ is alkyl, cycloalkyl, heterocycloalkyl, cycloalkylalkyl, heterocycloalkylalkyl, aryl, heteroaryl, arylalkyl or heteroarylalkyl;

$R_7$ is H, alkyl, cycloalkyl, heterocycloalkyl, cycloalkylalkyl, heterocycloalkylalkyl, aryl, heteroaryl, arylalkyl or heteroarylalkyl;

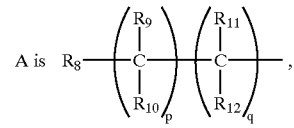

where p is 0, 1 or 2; and q is 1 or 2 but both p and q cannot be 2, or

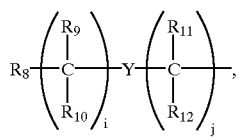

where i and j are each independently 0 or 1 but cannot both be 1, and Y is optionally substituted alkene, alkyne, or any 2 adjacent carbon atoms of a cycloalkyl or cycloheteroalkyl ring of 3–7 atoms;

$R_8$ is alkyl with two or more carbon atoms, cycloalkyl, heterocycloalkyl, cycloalkylalkyl, heterocycloalkylalkyl, aryl, heteroaryl, arylalkyl, heteroarylalkyl or $R_{13}$;

$R_9$, $R_{10}$, $R_{11}$ and $R_{12}$ are each independently H, alkyl, cycloalkyl, heterocycloalkyl, cycloalkylalkyl, heterocycloalkylalkyl, aryl, heteroaryl, arylalkyl, heteroarylalkyl, halo, or hydroxy, alkoxy, amino, $NR_{14}R_{15}$, thio or alkylthio, provided that only one hydroxy, alkoxy, amino, $NR_{14}R_{15}$, thio or alkylthio group is bonded to any one carbon atom;

$R_{13}$ is 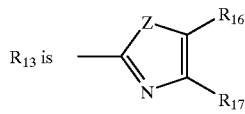

where Z is O, $NR_{18}$ or S;

$R_{16}$ and $R_{17}$ are each independently H, alkyl, cycloalkyl, heterocycloalkyl, cycloalkylalkyl, heterocycloalkylalkyl, aryl, heteroaryl, arylalkyl, heteroarylalkyl, halo, hydroxy, alkoxy, alkylcarbonyloxy, carboxy, alkyloxycarbonyl, amino, $NR_{19}R_{20}$, carbamoyl, ureido, thio or alkylthio;

$R_{14}$, $R_{15}$, $R_{18}$, $R_{19}$ and $R_{20}$ are each independently H, alkyl, cycloalkyl, heterocycloalkyl, cycloalkylalkyl, heterocycloalkylalkyl, aryl, heteroaryl, arylalkyl or heteroarylalkyl;

$R_1$ and $R_2$ are each independently hydrogen, fluorine or alkyl;

$R_3$ is aryl or heteroaryl;

$R_4$ is hydrogen, alkyl, cycloalkyl, aryl, cycloalkylalkyl, arylalkyl, heteroaryl, heteroarylalkyl, heterocycloalkyl, heterocycloalkylalkyl; or
 CO-alkyl, CO-cycloalkyl, CO-aryl, CO-alkyl-cycloalkyl, CO-alkyl-aryl, CO-heteroaryl, CO-alkyl-heteroaryl, CO-heterocycloalkyl, CO-alkyl-heterocycloalkyl; or
 CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or
 COO-alkyl, COO-cycloalkyl, COO-aryl, COO-alkyl-cycloalkyl, COO-alkyl-aryl, COO-heteroaryl, COO-alkyl-heteroaryl, COO-heterocycloalkyl, COO-alkyl-heterocycloalkyl; or
 $SO_2$-cycloalkyl, $SO_2$-aryl, $SO_2$-alkyl-cycloalkyl, $SO_2$-alkyl-aryl, $SO_2$-heteroaryl, $SO_2$-alkyl-heteroaryl, $SO_2$-heterocycloalkyl, $SO_2$-alkyl-heterocycloalkyl; or
 C(NCN)NH-alkyl, C(NCN)NH-cycloalkyl, C(NCN)NH-aryl, C(NCN)NH-alkyl-cycloalkyl, C(NCN)NH-alkyl-aryl, C(NCN)NH-heteroaryl, C(NCN)NH-alkyl-heteroaryl, C(NCN)NH-heterocycloalkyl, C(NCN)NH-alkyl-heterocycloalkyl; or
 $C(NNO_2)$NH-alkyl, $C(NNO_2)$NH-cycloalkyl, $C(NNO_2)$NH-aryl, $C(NNO_2)$NH-alkyl-cycloalkyl, $C(NNO_2)$NH-alkyl-aryl, $C(NNO_2)$NH-heteroaryl, $C(NNO_2)$NH-alkyl-heteroaryl, $C(NNO_2)$NH-heterocycloalkyl, $C(NNO_2)$NH-alkyl-heterocycloalkyl; or
 C(NH)NH-alkyl, C(NH)NH-cycloalkyl, C(NH)NH-aryl, C(NH)NH-alkyl-cycloalkyl, C(NH)NH-alkyl-aryl, C(NH)NH-heteroaryl, C(NH)NH-alkyl-heteroaryl, C(NH)NH-heterocycloalkyl, C(NH)NH-alkyl-heterocycloalkyl; or
 C(NH)NHCO-alkyl, C(NH)NHCO-cycloalkyl, C(NH)NHCO-aryl, C(NH)NHCO-alkyl-cycloalkyl, C(NH)NHCO-alkyl-aryl, C(NH)NHCO-heteroaryl, C(NH)NHCO-alkyl-heteroaryl, C(NH)NHCO-heterocycloalkyl, C(NH)NHCO-alkyl-heterocycloalkyl; or
 $C(NOR_{21})$NH-alkyl, $C(NOR_{21})$NU-cycloalkyl, $C(NOR_{21})$NH-aryl, $C(NOR_{21})$NH-alkyl-cycloalkyl, $C(NOR_{21})$NH-alkyl-aryl, $C(NOR_{21})$NH-heteroaryl, $C(NOR_{21})$NH-alkyl-heteroaryl, $C(NOR_{21})$NH-heterocycloalkyl, $C(NOR_{21})$NH-alkyl-heterocycloalkyl;

$R_5$ is hydrogen or alkyl;

$R_{21}$ is hydrogen, alkyl, cycloalkyl, aryl, cycloalkylalkyl, arylalkyl, heteroaryl, heteroarylalkyl, heterocycloalkyl or heterocycloalkylalkyl;

m is an integer of 0 to 2; and n is an integer of 1 to 3.

2. The method according to claim 1, wherein said pharmaceutically acceptable salt of said compound of formula I or II is a hydrochloride, a hydrobromide, a dihydrochloride, a sulfate, a trifluoroacetate, a tartrate, a fumarate, a succinate, a maleate, a citrate, a methanesulfonate, a bromate, or an iodate salt or a mixture thereof.

3. The method according to claim 1, wherein the mammalian specie is a human.

4. The method according to claim 1, wherein the compound is topically administered to the mammalian specie.

5. The method according to claim 4, wherein the compound is topically administered to the scalp.

6. The method according to claim 4, wherein the compound is topically administered in a form selected from the group consisting of a cream, a lotion, a solution, a dispersion, a shampoo, an ointment, a gel, a spot-on, a dust and an aerosol.

7. The method according to claim 1, wherein the compound is administered prior to chemotherapy or radiotherapy treatment.

8. The method according to claim 1, wherein the alopecia is induced by chemotherapy.

9. The method according to claim 1, wherein the alopecia is induced by radiotherapy.

10. The method according to claim 1, wherein the compound is administered in the form of a liposome delivery system.

11. The method according to claim 10, wherein the liposome delivery system is topically administered.

12. The method according to claim 1, wherein the compound is administered in the form of a pharmaceutical composition comprising the compound and a pharmaceutically acceptable carrier.

13. The method according to claim 1, wherein the compound is a compound of formula I.

14. The method according to claim 13, wherein said pharmaceutically acceptable salt of said compound of formula I is a hydrochloride, a hydrobromide, a dihydrochloride, a sulfate, a trifluoroacetate, a tartrate, a fumarate, a succinate, a maleate, a citrate, a methanesulfonate, a bromate, or an iodate salt or a mixture thereof.

15. The method according to claim 13, wherein R is $R_6$, $COR_7$ or $CONR_6R_7$;

$R_6$ is alkyl, aryl, heteroaryl, arylalkyl or heteroarylalkyl;

$R_7$ is H, alkyl, aryl, heteroaryl, arylalkyl or heteroarylalkyl;

A is 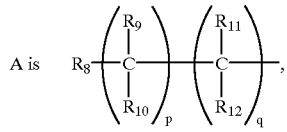

where p is 0, 1 or 2; and q is 1 or 2, or

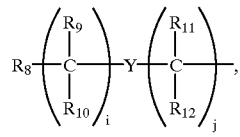

where i and j are each independently 0 or 1 but cannot both be 1, and Y is optionally substituted alkene, alkyne, or any two adjacent carbon atoms of a cycloalkyl ring;

$R_8$ is alkyl with two or more carbon atoms, aryl, heteroaryl or $R_{13}$;

$R_9$, $R_{10}$, $R_{11}$ and $R_{12}$ are each independently H or alkyl;

$R_{13}$ is 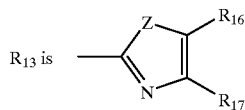

where Z is O; and $R_{16}$ and $R_{17}$ are each independently H, alkyl or cycloalkyl.

16. The method according to claim 13, wherein

R is $COR_7$;

$R_7$ is H, alkyl, heteroaryl, arylalkyl or heteroarylalkyl;

A is 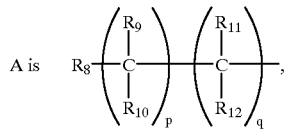

where p is 0 or 1; and q is 1, or

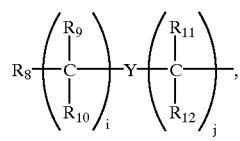

where i and j are each independently 0 or 1 but cannot both be 1, and Y is an optionally substituted alkene;

$R_8$ is $R_{13}$;

$R_9$, $R_{10}$, $R_{11}$ and $R_{12}$ are each independently H or alkyl;

$R_{13}$ is 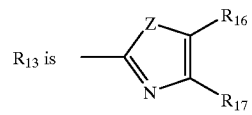

where Z is O; and $R_{16}$ and $R_{17}$ are each independently H, alkyl or cycloalkyl.

17. The method according to claim 13, wherein

R is $COR_7$;

$R_7$ is alkyl, arylalkyl, heteroaryl or heteroarylalkyl;

A is 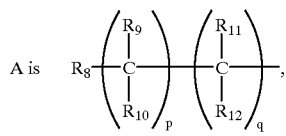

where p is 0 or 1; and q is 1;

$R_9$, $R_{10}$, $R_{11}$ and $R_{12}$ are each independently H or alkyl;

$R_8$ is $R_{13}$;

$R_{13}$ is 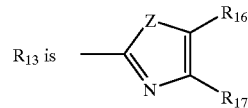

where Z is O;

$R_{16}$ is alkyl or cycloalkyl; and $R_{17}$ is H.

18. The method according to claim 13, wherein

R is $COR_7$;

$R_7$ is alkyl, arylalkyl, heteroaryl or heteroarylalkyl;

A is 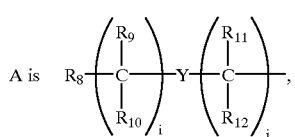

where i and j are each independently 0 or 1 but cannot both be 1, and Y is an optionally substituted alkene or alkyne;

$R_8$ is $R_{13}$;

$R_9$, $R_{10}$, $R_{11}$ and $R_{12}$ are each independently H or alkyl;

$R_{13}$ is 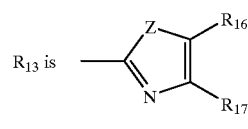

where Z is O;

$R_{16}$ is alkyl or cycloalkyl; and $R_{17}$ is H.

19. The method according to claim 13, wherein

R is $R_6$;

$R_6$ is alkyl, aryl, heteroaryl, arylalkyl or heteroarylalkyl;

A is 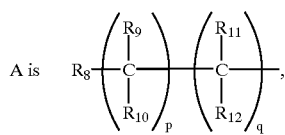

where p is 0 or 1; and q is 1, or

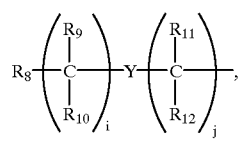

where i and j are each independently 0 or 1 but cannot both be 1, and Y is an optionally substituted alkene;

$R_8$ is $R_{13}$;

$R_9$, $R_{10}$, $R_{11}$ and $R_{12}$ are each independently H or alkyl;

$R_{13}$ is 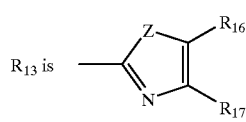

where Z is O; and $R_{16}$ and $R_{17}$ are each independently H, alkyl or cycloalkyl.

20. The method according to claim 13, wherein

R is $R_6$;

$R_6$ is alkyl, aryl, heteroaryl, arylalkyl or heteroarylalkyl;

A is 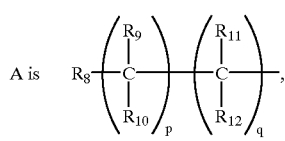

where p is 0 or 1; and q is 1;

$R_9$, $R_{10}$, $R_{11}$ and $R_{12}$ are each independently H or alkyl;

$R_8$ is $R_{13}$;

$R_{13}$ is 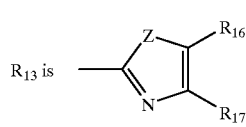

where Z is O;

$R_{16}$ is alkyl or cycloalkyl; and $R_{17}$ is H.

21. The method according to claim 13, wherein

R is $R_6$;

$R_6$ is alkyl, aryl, heteroaryl, arylalkyl or heteroarylalkyl;

A is 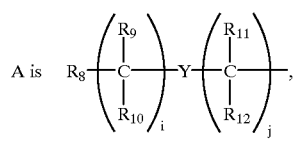

where i and j are each independently 0 or 1 but cannot both be 1, and Y is an optionally substituted alkene or alkyne;

$R_8$ is $R_{13}$;

$R_9$, $R_{10}$, $R_{11}$ and $R_{12}$ are each independently H or alkyl;

$R_{13}$ is 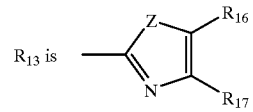

where Z is O;

$R_{16}$ is alkyl or cycloalkyl; and $R_{17}$ is H.

22. The method according to claim 13, wherein

R is $CONR_6R_7$;

$R_6$ is alkyl, heteroaryl, arylalkyl or heteroarylalkyl;

$R_7$ is H, alkyl, heteroaryl, arylalkyl or heteroarylalkyl;

A is 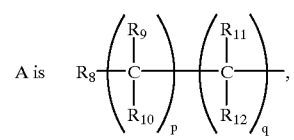

where p is 0 or 1; and q is 1, or

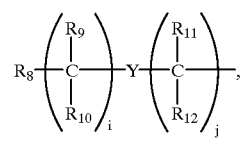

where i and j are each independently 0 or 1 but cannot both be 1, and Y is an optionally substituted alkene;

$R_8$ is $R_{13}$;

$R_9$, $R_{10}$, $R_{11}$ and $R_{12}$ are each independently H or alkyl;

$R_{13}$ is 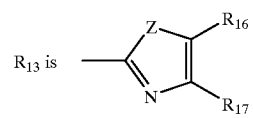

where Z is O; and $R_{16}$ and $R_{17}$ are each independently H, alkyl or cycloalkyl.

23. The method according to claim 13, wherein

R is $CONR_6R_7$;

$R_6$ is alkyl, arylalkyl, heteroaryl or heteroarylalkyl;

$R_7$ is H, alkyl, heteroaryl, arylalkyl or heteroarylalkyl;

A is 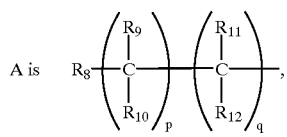

where p is 0 or 1; and q is 1;

$R_8$ is $R_{13}$;

$R_9$, $R_{10}$, $R_{11}$ and $R_{12}$ are each independently H or alkyl;

$R_{13}$ is 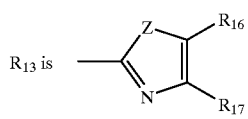

where Z is O;

$R_{16}$ is alkyl or cycloalkyl; and $R_{17}$ is H.

24. The method according to claim 13, wherein

R is $CONR_6R_7$;

$R_6$ is alkyl, arylalkyl, heteroaryl or heteroarylalkyl;

$R_7$ is H, alkyl, heteroaryl, arylalkyl or heteroarylalkyl;

A is 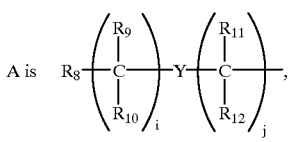

where i and j are each independently 0 or 1 but cannot both be 1, and Y is an optionally substituted alkene or alkyne;

$R_8$ is $R_{13}$;

$R_9$, $R_{10}$, $R_{11}$ and $R_{12}$ are each independently H or alkyl;

$R_{13}$ is 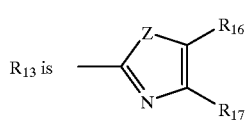

where Z is O;

$R_{16}$ is alkyl or cycloalkyl; and $R_{17}$ is H.

25. The method according to claim 1, wherein the compound is a compound of formnula II.

26. The method according to claim 25, wherein said pharmaceutically acceptable salt of said compound of formula II is a hydrochloride, a hydrobromide, a dihydrochloride, a sulfate, a trifluoroacetate, a tartrate, a fumarate, a succinate, a maleate, a citrate, a methanesulfonate, a bromate, or an iodate salt or a mixture thereof.

27. The method according to claim 25, wherein $R_1$ and $R_2$ are each independently hydrogen or alkyl;

$R_3$ is 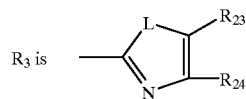

where L is oxygen, sulfur or $NR_{25}$;

$R_4$ is hydrogen, alkyl, cycloalkyl, aryl, cycloalkylalkyl, arylalkyl, heteroaryl, heteroarylalkyl, heterocycloalkyl, heterocycloalkylalkyl; or CO-alkyl, CO-cycloalkyl, CO-aryl, CO-alkyl-cycloalkyl, CO-alkyl-aryl, CO-heteroaryl, CO-alkyl-heteroaryl, CO-heterocycloalkyl, CO-alkyl-heterocycloalkyl; or CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or COO-alkyl, COO-cycloalkyl, COO-aryl, COO-alkyl-cycloalkyl, COO-alkyl-aryl, COO-heteroaryl, COO-alkyl-heteroaryl, COO-heterocycloalkyl, COO-alkyl-heterocycloalkyl; or $SO_2$-cycloalkyl, $SO_2$-aryl, $SO_2$-alkyl-cycloalkyl, $SO_2$-alkyl-aryl, $SO_2$-heteroaryl, $SO_2$-alkyl-heteroaryl, $SO_2$-heterocycloalkyl, $SO_2$-alkyl-heterocycloalkyl; or C(NCN)NH-alkyl, C(NCN)NH-cycloalkyl, C(NCN)NH-aryl, C(NCN)NH-alkyl-cycloalkyl, C(NCN)NH-alkyl-aryl, C(NCN)NH-heteroaryl, C(NCN)NH-alkyl-heteroaryl, C(NCN)NH-heterocycloalkyl, C(NCN)NH-alkyl-heterocycloalkyl; or $C(NNO_2)$NH-alkyl, $C(NNO_2)$NH-cycloalkyl, $C(NNO_2)$NH-aryl, $C(NNO_2)$NH-alkyl-cycloalkyl, $C(NNO_2)$NH-alkyl-aryl, $C(NNO_2)$NH-heteroaryl, $C(NNO_2)$NH-alkyl-heteroaryl, $C(NNO_2)$NH-heterocycloalkyl, $C(NNO_2)$NH-alkyl-heterocycloalkyl; or C(NH)NH-alkyl, C(NH)NH-cycloalkyl, C(NH)NH-aryl, C(NH)NH-alkyl-cycloalkyl, C(NH)NH-alkyl-aryl, C(NH)NH-heteroaryl, C(NH)NH-alkyl-heteroaryl, C(NH)NH-heterocycloalkyl, C(NH)NH-alkyl-heterocycloalkyl; or C(NH)NHCO-alkyl, C(NH)NHCO-cycloalkyl, C(NH)NHCO-aryl, C(NH)NHCO-alkyl-cycloalkyl, C(NH)NHCO-alkyl-aryl, C(NH)NHCO-heteroaryl, C(NH)NHCO-alkyl-heteroaryl, C(NH)NHCO-heterocycloalkyl, C(NH)NHCO-alkyl-heterocycloalkyl; or $C(NOR_{21})$NH-alkyl, $C(NOR_{21})$NH-cycloalkyl, $C(NOR_{21})$NH-aryl, $C(NOR_{21})$NH-alkyl-cycloalkyl, $C(NOR_{21})$NH-alkyl-aryl, $C(NOR_{21})$NH-heteroaryl, $C(NOR_{21})$NH-alkyl-heteroaryl, $C(NOR_{21})$NH-heterocycloalkyl, $C(NOR_{21})$NH-alkyl-heterocycloalkyl;

$R_5$ is hydrogen or alkyl;

$R_{21}$ is hydrogen, alkyl, cycloalkyl, aryl, cycloalkylalkyl, arylalkyl, heteroaryl, heteroarylalkyl, heterocycloalkyl or heterocycloalkylalkyl;

$R_{23}$ and $R_{24}$ are each independently hydrogen, alkyl, substituted alkyl, cycloalkyl, aryl, substituted aryl, cycloalkylalkyl, arylalkyl, heteroaryl, substituted heteroaryl, heteroarylalkyl, heterocycloalkyl or heterocycloalkylalkyl;

$R_{25}$ is hydrogen, alkyl, cycloalkyl, aryl, alkylcycloalkyl, arylalkyl, heteroaryl, heteroarylalkyl, heterocycloalkyl or heterocycloalkylalkyl;

m is an integer of 0 to 2; and
n is an integer of 1 to 3.

28. The method according to claim 25, wherein
$R_1$ and $R_2$ are each independently hydrogen or alkyl;

$R_3$ is 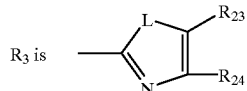

where L is oxygen;
$R_4$ is hydrogen, alkyl, cycloalkyl, aryl, cycloalkylalkyl, arylalkyl, heteroaryl, heteroarylalkyl, heterocycloalkyl, heterocycloalkylalkyl; or
CO-alkyl, CO-cycloalkyl, CO-aryl, CO-alkyl-cycloalkyl, CO-alkyl-aryl, CO-heteroaryl, CO-alkyl-heteroaryl, CO-heterocycloalkyl, CO-alkyl-heterocycloalkyl; or
CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or
COO-alkyl, COO-cycloalkyl, COO-aryl, COO-alkyl-cycloalkyl, COO-alkyl-aryl, COO-heteroaryl, COO-alkyl-heteroaryl, COO-heterocycloalkyl, COO-alkyl-heterocycloalkyl; or
$SO_2$-cycloalkyl, $SO_2$-aryl, $SO_2$-alkyl-cycloalkyl, $SO_2$-alkyl-aryl, $SO_2$-heteroaryl, $SO_2$-alkyl-heteroaryl, $SO_2$-heterocycloalkyl, $SO_2$-alkyl-heterocycloalkyl; or
C(NCN)NH-alkyl, C(NCN)NH-cycloalkyl, C(NCN)NH-aryl, C(NCN)NH-alkyl-cycloalkyl, C(NCN)NH-alkyl-aryl, C(NCN)NH-heteroaryl, C(NCN)NH-alkyl-heteroaryl, C(NCN)NH-heterocycloalkyl, C(NCN)NH-alkyl-heterocycloalkyl; or
$C(NNO_2)$NH-alkyl, $C(NNO_2)$NH-cycloalkyl, $C(NNO_2)$NH-aryl, $C(NNO_2)$NH-alkyl-cycloalkyl, $C(NNO_2)$NH-alkyl-aryl, $C(NNO_2)$NH-heteroaryl, $C(NNO_2)$NH-alkyl-heteroaryl, $C(NNO_2)$NH-heterocycloalkyl, $C(NNO_2)$NH-alkyl-heterocycloalkyl; or
C(NH)NH-alkyl, C(NH)NH-cycloalkyl, C(NH)NH-aryl, C(NH)NH-alkyl-cycloalkyl, C(NH)NH-alkyl-aryl, C(NH)NH-heteroaryl, C(NH)NH-alkyl-heteroaryl, C(NH)NH-heterocycloalkyl, C(NH)NH-alkyl-heterocycloalkyl; or
C(NH)NHCO-alkyl, C(NH)NHCO-cycloalkyl, C(NH)NHCO-aryl, C(NH)NHCO-alkyl-cycloalkyl, C(NH)NHCO-alkyl-aryl, C(NH)NHCO-heteroaryl, C(NH)NHCO-alkyl-heteroaryl, C(NH)NHCO-heterocycloalkyl, C(NH)NHCO-alkyl-heterocycloalkyl; or
$C(NOR_{21})$NH-alkyl, $C(NOR_{21})$NH-cycloalkyl, $C(NOR_{21})$NH-aryl, $C(NOR_{21})$NH-alkyl-cycloalkyl, $C(NOR_{21})$NH-alkyl-aryl, $C(NOR_{21})$NH-heteroaryl, $C(NOR_{21})$NH-alkyl-heteroaryl, $C(NOR_{21})$NH-heterocycloalkyl, $C(NOR_{21})$NH-alkyl-heterocycloalkyl;
$R_5$ is hydrogen;
$R_{21}$ is hydrogen, alkyl, cycloalkyl, aryl, cycloalkylalkyl, arylalkyl, heteroaryl, heteroarylalkyl, heterocycloalkyl or heterocycloalkylalkyl;
$R_{23}$ and $R_{24}$ are each independently hydrogen, alkyl, substituted alkyl, cycloalkyl, aryl, substituted aryl, cycloalkylalkyl, arylalkyl, heteroaryl, substituted heteroaryl, heteroarylalkyl, heterocycloalkyl or heterocycloalkylalkyl;

m is an integer of 0 to 2; and
n is an integer of 1 to 3.

29. The method according to claim 25, wherein
$R_1$ and $R_2$ are each independently hydrogen or alkyl;

$R_3$ is 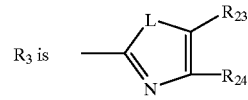

where L is sulfur;
$R_4$ is hydrogen, alkyl, cycloalkyl, aryl, cycloalkylalkyl, arylalkyl, heteroaryl, heteroarylalkyl, heterocycloalkyl, heterocycloalkylalkyl; or
CO-alkyl, CO-cycloalkyl, CO-aryl, CO-alkyl-cycloalkyl, CO-alkyl-aryl, CO-heteroaryl, CO-alkyl-heteroaryl, CO-heterocycloalkyl, CO-alkyl-heterocycloalkyl; or
CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or
COO-alkyl, COO-cycloalkyl, COO-aryl, COO-alkyl-cycloalkyl, COO-alkyl-aryl, COO-heteroaryl, COO-alkyl-heteroaryl, COO-heterocycloalkyl, COO-alkyl-heterocycloalkyl; or
$SO_2$-cycloalkyl, $SO_2$-aryl, $SO_2$-alkyl-cycloalkyl, $SO_2$-alkyl-aryl, $SO_2$-heteroaryl, $SO_2$-alkyl-heteroaryl, $SO_2$-heterocycloalkyl, $SO_2$-alkyl-heterocycloalkyl; or
C(NCN)NH-alkyl, C(NCN)NH-cycloalkyl, C(NCN)NH-aryl, C(NCN)NH-alkyl-cycloalkyl, C(NCN)NH-alkyl-aryl, C(NCN)NH-heteroaryl, C(NCN)NH-alkyl-heteroaryl, C(NCN)NH-heterocycloalkyl, C(NCN)NH-alkyl-heterocycloalkyl; or
$C(NNO_2)$NH-alkyl, $C(NNO_2)$NH-cycloalkyl, $C(NNO_2)$NH-aryl, $C(NNO_2)$NH-alkyl-cycloalkyl, $C(NNO_2)$N H-alkyl-aryl, $C(NNO_2)$N -heteroaryl, $C(NNO_2)$NH-alkyl-heteroaryl, $C(NNO_2)$NH-heterocycloalkyl, $C(NNO_2)$NH-alkyl-heterocycloalkyl; or
C(NH)NH-alkyl, C(NH)NH-cycloalkyl, C(NH)NH-aryl, C(NH)NH-alkyl-cycloalkyl, C(NH)NH-alkyl-aryl, C(NH)NH-heteroaryl, C(NH)NH-alkyl-heteroaryl, C(NH)NH-heterocycloalkyl, C(NH)NH-alkyl-heterocycloalkyl; or
C(NH)NHCO-alkyl, C(NH)NHCO-cycloalkyl, C(NH)NHCO-aryl, C(NH)NHCO-alkyl-cycloalkyl, C(NH)NHCO-alkyl-aryl, C(NH)NHCO-heteroaryl, C(NH)NHCO-alkyl-heteroaryl, C(NH)NHCO-heterocycloalkyl, C(NH)NHCO-alkyl-heterocycloalkyl; or
$C(NOR_{21})$NH-alkyl, $C(NOR_{21})$NH-cycloalkyl, $C(NOR_{21})$NH-aryl, $C(NOR_{21})$NH-alkyl-cycloalkyl, $C(NOR_{21})$NH-alkyl-aryl, $C(NOR_{21})$NH-heteroaryl, $C(NOR_{21})$NH-alkyl-heteroaryl, $C(NOR_{21})$NH-heterocycloalkyl, $C(NOR_{21})$NH-alkyl-heterocycloalkyl;
$R_5$ is hydrogen;
$R_{21}$ is hydrogen, alkyl, cycloalkyl, aryl, cycloalkylalkyl, arylalkyl, heteroaryl, heteroarylalkyl, heterocycloalkyl or heterocycloalkylalkyl;
$R_{23}$ and $R_{24}$ are each independently hydrogen, alkyl, substituted alkyl, cycloalkyl, aryl, substituted aryl, cycloalkylalkyl, arylalkyl, heteroaryl, substituted heteroaryl, heteroarylalkyl, heterocycloalkyl or heterocycloalkylalkyl;

m is an integer of 0 to 2; and n is an integer of 1 to 3.

30. The method according to claim 25, wherein
R$_1$ and R$_2$ are each independently hydrogen or alkyl;

R$_3$ is 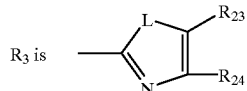

where L is NR$_{25}$;

R$_4$ is hydrogen, alkyl, cycloalkyl, aryl, cycloalkylalkyl, arylalkyl, heteroaryl, heteroarylalkyl, heterocycloalkyl, heterocycloalkylalkyl; or CO-alkyl, CO-cycloalkyl, CO-aryl, CO-alkyl-cycloalkyl, CO-alkyl-aryl, CO-heteroaryl, CO-alkyl-heteroaryl, CO-heterocycloalkyl, CO-alkyl-heterocycloalkyl; or CONH-alkyl, CONH-cycloalkyl, CONH-aryl, CONH-alkyl-cycloalkyl, CONH-alkyl-aryl, CONH-heteroaryl, CONH-alkyl-heteroaryl, CONH-heterocycloalkyl, CONH-alkyl-heterocycloalkyl; or COO-alkyl, COO-cycloalkyl, COO-aryl, COO-alkyl-cycloalkyl, COO-alkyl-aryl, COO-heteroaryl, COO-alkyl-heteroaryl, COO-heterocycloalkyl, COO-alkyl-heterocycloalkyl; or SO$_2$-cycloalkyl, SO$_2$-aryl, SO$_2$-alkyl-cycloalkyl, SO$_2$-alkyl-aryl, SO$_2$-heteroaryl, SO$_2$-alkyl-heteroaryl, SO$_2$-heterocycloalkyl, SO$_2$-alkyl-heterocycloalkyl; or C(NCN)NH-alkyl, C(NCN)NH-cycloalkyl, C(NCN)NH-aryl, C(NCN)NH-alkyl-cycloalkyl, C(NCN)NH-alkyl-aryl, C(NCN)NH-heteroaryl, C(NCN)NH-alkyl-heteroaryl, C(NCN)NH-heterocycloalkyl, C(NCN)NH-alkyl-heterocycloalkyl; or C(NNO$_2$)NH-alkyl, C(NNO$_2$)NH-cycloalkyl, C(NNO$_2$)NH-aryl, C(NNO$_2$)NH-alkyl-cycloalkyl, C(NNO$_2$)NH-alkyl-aryl, C(NNO$_2$)NH-heteroaryl, C(NNO$_2$)NH-alkyl-heteroaryl, C(NNO$_2$)NH-heterocycloalkyl, C(NNO$_2$)NH-alkyl-heterocycloalkyl; or C(NH)NH-alkyl, C(NH)NH-cycloalkyl, C(NH)NH-aryl, C(NH)NH-alkyl-cycloalkyl, C(NH)NH-alkyl-aryl, C(NH)NH-heteroaryl, C(NH)NH-alkyl-heteroaryl, C(NH)NH-heterocycloalkyl, C(NH)NH-alkyl-heterocycloalkyl; or C(NH)NHCO-alkyl, C(NH)NHCO-cycloalkyl, C(NH)NHCO-aryl, C(NH)NHCO-alkyl-cycloalkyl, C(NH)NHCO-alkyl-aryl, C(NH)NHCO-heteroaryl, C(NH)NHCO-alkyl-heteroaryl, C(NH)NHCO-heterocycloalkyl, C(NH)NHCO-alkyl-heterocycloalkyl; or C(NOR$_{21}$)NH-alkyl, C(NOR$_{21}$)NH-cycloalkyl, C(NOR$_{21}$)NH-aryl, C(NOR$_{21}$)NH-alkyl-cycloalkyl, C(NOR$_{21}$)NH-alkyl-aryl, C(NOR$_{21}$)NH-heteroaryl, C(NOR$_{21}$)NH-alkyl-heteroaryl, C(NOR$_{21}$)NH-heterocycloalkyl, C(NOR$_{21}$)NH-alkyl-heterocycloalkyl;

R$_5$ is hydrogen;

R$_{21}$ is hydrogen, alkyl, cycloalkyl, aryl, cycloalkylalkyl, arylalkyl, heteroaryl, heteroarylalkyl, heterocycloalkyl or heterocycloalkylalkyl;

R$_{23}$ and R$_{24}$ are each independently hydrogen, alkyl, substituted alkyl, cycloalkyl, aryl, substituted aryl, cycloalkylalkyl, arylalkyl, heteroaryl, substituted heteroaryl, heteroarylalkyl, heterocycloalkyl or heterocycloalkylalkyl;

R$_{25}$ is hydrogen, alkyl, cycloalkyl, aryl, cycloalkylalkyl, arylalkyl, heteroaryl, heteroarylalkyl, heterocycloalkyl or heterocycloalkylalkyl;

m is an integer of 0 to 2; and n is an integer of 1 to 3.

31. The method according to claim 25, wherein
R$_1$ and R$_2$ are each independently hydrogen or alkyl;

R$_3$ is 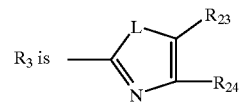

where L is oxygen;

R$_4$ is aryl, heteroaryl, CO-alkyl, CO-alkyl-aryl, CO-cycloalkyl, CO-alkyl-heteroaryl, CO-alkyl-heteroalkyl, CO-alkyl-heterocycloalkyl, CONH-alkyl, CONH-alkyl-aryl, CONH-cycloalkyl or CONH-alkyl-heterocycloalkyl;

R$_5$ is hydrogen;

R$_{23}$ and R$_{24}$ are hydrogen;

m is the integer 0; and n is the integer 1.

32. The method according to claim 25, wherein
R$_1$ and R$_2$ are independently hydrogen or alkyl;

R$_3$ is 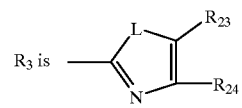

where L is oxygen;

R$_4$ is aryl, heteroaryl, CO-alkyl, CO-alkyl-aryl, CO-alkyl-heteroalkyl, CO-cycloalkyl, CO-alkyl-heterocycloalkyl, CO-alkyl-heteroaryl, CONH-alkyl, CONH-alkyl-aryl, CONH-cycloalkyl or CONH-alkyl-heterocycloalkyl;

R$_5$ is hydrogen;

R$_{23}$ is alkyl;

R$_{24}$ is hydrogen;

m is the integer 0; and n is the integer 1.

33. The method according to claim 25, wherein R$_1$ and R$_2$ are independently hydrogen or alkyl;

R$_3$ is 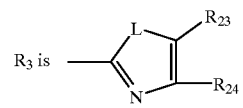

where L is sulfur;

R$_4$ is aryl, heteroaryl, CO-alkyl, CO-alkyl-aryl, CO-alkyl-heteroalkyl, CO-cycloalkyl, CO-alkyl-heterocycloalkyl, CO-alkyl-heteroaryl, CONH-alkyl, CONH-alkyl-aryl, CONH-cycloalkyl or CONH-alkyl-heterocycloalkyl;

R$_5$ is hydrogen;

R$_{23}$ is alkyl;

R$_{24}$ is hydrogen;

m is the integer 0; and n is the integer 1.

34. The method according to claim 25, wherein $R_1$ and $R_2$ are independently hydrogen or alkyl;

$R_3$ is 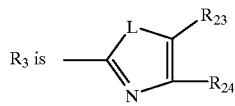

where L is $NR_{25}$;
$R_4$ is aryl, heteroaryl, CO-alkyl, CO-alkyl-aryl, CO-alkyl-heteroalkyl, CO-cycloalkyl, CO-alkyl-heterocycloalkyl, CO-alkyl-heteroaryl, CONH-alkyl, CONH-alkyl-aryl, CONH-cycloalkyl or CONH-alkyl-heterocycloalkyl;
$R_5$ is hydrogen;
$R_{23}$ is alkyl;
$R_{24}$ is hydrogen;
$R_{25}$ is hydrogen, alkyl, cycloalkyl, aryl, alkyl-cycloalkyl, alkyl-aryl, heteroaryl, alkyl-heteroaryl, heterocycloalkyl or alkyl-heterocycloalkyl;
m is the integer 0; and
n is the integer 1.

35. The method according to claim 25, wherein $R_1$ and $R_2$ are independently hydrogen or alkyl;

$R_3$ is 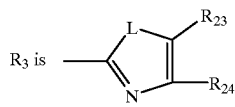

where L is $NR_{25}$;
$R_4$ is aryl, heteroaryl, CO-alkyl, CO-alkyl-aryl, CO-cycloalkyl, CO-alkyl-heteroaryl, CO-alkyl-heteroalkyl, CO-alkyl-heterocycloalkyl, CONH-alkyl, CONH-alkyl-aryl, CONH-cycloalkyl or CONH-alkyl-heterocycloalkyl;
$R_5$ is hydrogen;
$R_{23}$ is hydrogen;
$R_{24}$ is alkyl;
$R_{25}$ is hydrogen;
m is the integer 0; and
n is the integer 1.

36. The method of claim 25, wherein the compound is a compound of formula IIj:

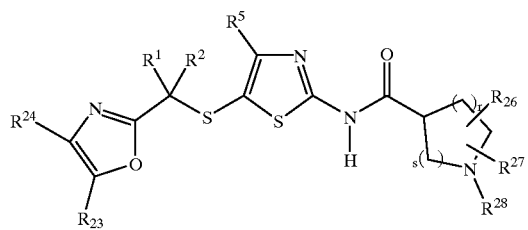

or a pharmaceutically acceptable salt thereof, wherein:
$R^1$, $R^2$, and $R^5$ are independently hydrogen or alkyl;
$R^{23}$ is alkyl, aryl, or heteroaryl;
$R^{24}$ is hydrogen, alkyl, aryl, or heteroaryl;
$R^{26}$ and $R^{27}$ are independently hydrogen, alkyl, aryl, heteroaryl, halogen, hydroxy, or alkoxy;

$R^{28}$ is hydrogen, alkyl, cycloalkyl, aryl, heteroaryl, $CONR^{29}R^{30}$, $COR^{31}$, or $COOR^{32}$;
$R^{29}$, $R^{30}$, $R^{31}$ and $R^{32}$ are independently hydrogen, alkyl, or aryl;
r is an integer ranging from 0 to 5; and
s is an integer ranging from 0 to 5.

37. The method of claim 25, wherein the compound is a compound of formula IIk:

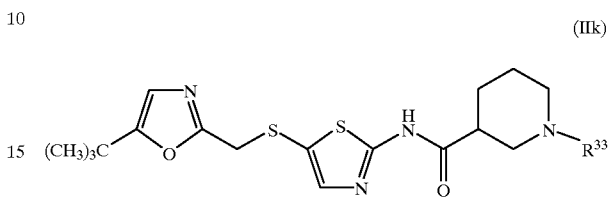

or a pharmaceutically acceptable salt thereof, wherein $R^{33}$ is hydrogen, alkyl, or cycloalkyl.

38. The method of claim 25, wherein the compound is a compound of formula IIl:

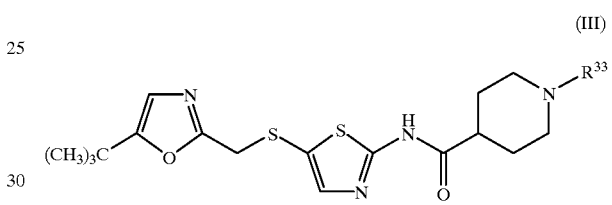

or a pharmaceutically acceptable salt thereof, wherein $R^{33}$ is hydrogen, alkyl, or cycloalkyl.

39. The method of claim 25, wherein the compound is a compound of formula IIm:

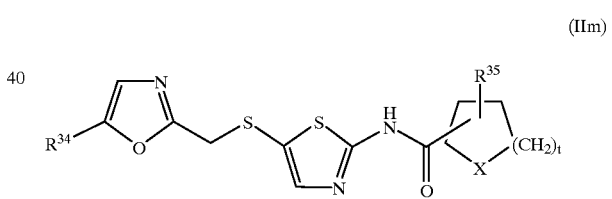

or a pharmaceutically acceptable salt thereof, wherein
$R^{34}$ is alkyl;
$R^{35}$ is hydrogen or alkyl;
X is $NR^{36}$ or $CHNR^{36}R^{37}$;
$R^{36}$ and $R^{37}$ are independently hydrogen, alkyl, or cycloalkyl; and
t is 0, 1, 2 or 3.

40. The method of claim 25, wherein the compound is a compound of formula IIn:

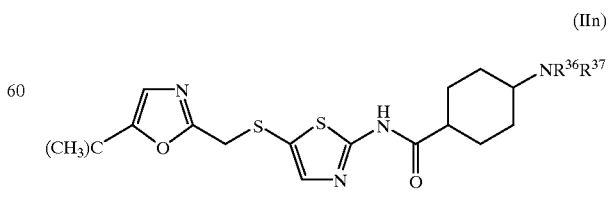

or a pharmaceutically acceptable salt thereof, wherein $R^{36}$ and $R^{37}$ are independently hydrogen, alkyl, or cycloalkyl.

41. The method of claim 25, wherein the compound is:

N-[5-[[[5-(1,1-dimethylethyl)-2-oxazolyl]methyl]thio]-2-thiazolyl]-4-piperidinecarboxamide;

(±)-N-[5-[[[5-(1,1-dimethylethyl)-2-oxazolyl]methyl]thio]-2-thiazolyl]-3-piperidinecarboxamide;

(±)-1-(2,3-dihydroxypropyl)-N-[5-[[[5-(1,1-dimethylethyl)-2-oxazolyl]methyl]thio]-2-thiazolyl]-4-piperidinecarboxamide;

N-[5-[[[5-(1,1-dimethylethyl)-2-oxazolyl]methyl]thio]-2-thiazolyl]-1-(1-methylethyl)-4-piperidinecarboxamide;

1-cyclopropyl-N-[5-[[[5-(1,1-dimethylethyl)-2-oxazolyl]methyl]thio]-2-thiazolyl]-4-piperidinecarboxamide;

N-[5-[[[5-(1,1-dimethylethyl)-2-oxazolyl]methyl]thio]-2-thiazolyl]-1-(2-hydroxyethyl)-4-piperidinecarboxamide;

(R)-N-[5-[[[5-(1,1-dimethylethyl)-2-oxazolyl]methyl]thio]-2-thiazolyl]-3-piperidinecarboxamide;

(S)-N-[5-[[[5-(1,1-dimethylethyl)-2-oxazolyl]methyl]thio]-2-thiazolyl]-3-piperidinecarboxamide;

cis-4-amino-N-[5-[[[5-(1,1-dimethylethyl)-2-oxazolyl]methyl]thio ]-2-thiazolyl]cyclohexylcarboxamide; or trans-4-amino-N-[5-[[[5-(1,1-dimethylethyl)-2-oxazolyl]methyl]thio]-2-thiazolyl]cyclohexylcarboxamide, or a pharmaceutically acceptable salt thereof.

42. The method of claim 38, wherein the compound is a compound of formula III

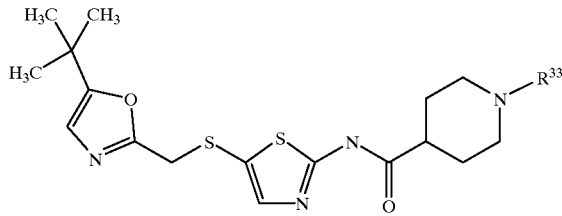

or a pharmaceutically acceptable salt thereof, wherein $R^{33}$ is hydrogen.

43. The method of claim 42, wherein said salt is a hydrochloride, a hydrobromide, a dihydrochloride, a sulfate, a trifluoroacetate, a tartrate, a fumarate, a succinate, a maleate, a citrate, a methanesulfonate, a bromate, or an iodate salt.

* * * * *

UNITED STATES PATENT AND TRADEMARK OFFICE
CERTIFICATE OF CORRECTION

PATENT NO.  : 6,534,531 B2
DATED       : March 18, 2003
INVENTOR(S) : Kimball et al.

It is certified that error appears in the above-identified patent and that said Letters Patent is hereby corrected as shown below:

Column 48,
Line 20, "NU-cycloalkyl" should read -- NH-cycloalkyl --

Signed and Sealed this

Twelfth Day of October, 2004

JON W. DUDAS
*Director of the United States Patent and Trademark Office*